(12) United States Patent
Hu

(10) Patent No.: US 8,066,914 B2
(45) Date of Patent: Nov. 29, 2011

(54) 7-ETHYNYL-2,4,9-TRITHIAADAMANTANE AND RELATED METHODS

(75) Inventor: Jun Hu, Fairlawn, OH (US)

(73) Assignee: University of Akron, Akron, OH (US)

( * ) Notice: Subject to any disclaimer, the term of this patent is extended or adjusted under 35 U.S.C. 154(b) by 582 days.

(21) Appl. No.: 12/262,871

(22) Filed: Oct. 31, 2008

(65) Prior Publication Data

US 2010/0072425 A1 Mar. 25, 2010

Related U.S. Application Data

(62) Division of application No. 10/562,088, filed on Mar. 17, 2008, now Pat. No. 7,501,529.

(51) Int. Cl.
*H01B 1/10* (2006.01)
*H01L 29/04* (2006.01)
*H01L 29/12* (2006.01)

(52) U.S. Cl. .................. 252/519.3; 257/40
(58) Field of Classification Search ............ 252/519.3; 257/40
See application file for complete search history.

(56) References Cited

U.S. PATENT DOCUMENTS

| 3,719,710 A | 3/1973 | Thomas et al. |
| 4,202,892 A | 5/1980 | Weiner et al. |
| 5,045,551 A | 9/1991 | Chandraratna et al. |
| 5,475,341 A | 12/1995 | Reed |
| 5,589,692 A | 12/1996 | Reed |
| 6,495,323 B1 | 12/2002 | Kayyem et al. |

OTHER PUBLICATIONS

Bax, A., et al., "Practical Aspects of Two-Dimensional Transverse NOE Spectroscopy", Journal of Magnetic Resonance, 63, 207-213 (1985).
Benesi, H.A., et al., "A Spectrophotometric Investigation of the Interaction of Iodine with Aromatic Hydrocarbons", Journal of American Chemical Society, 1959, 71 (8), 2703-2707.
Kittredge, Kevin W., et al., "a-Helical Polypeptide Films Grown From Sulfide or Thiol Linkers on Gold Surfaces", Helvetica Chimica Acta, 2002, 85, 788-798.

*Primary Examiner* — Bernard Dentz
(74) *Attorney, Agent, or Firm* — Renner, Kenner, Greive, Bobak, Taylor & Weber

(57) ABSTRACT

7-ethynyl-2,4,9-trithiaadamantane and related methods are presented. Manufacturing 7-ethynyl-2,4,9-trithiaadamantane includes the steps of: (1) reducing alkyl 2,4,9-trithiaadamantane-7-carboxylate to produce 7-hydroxymethyl-2,4,9-trithiaadamantane; (2) oxidizing 7-hydroxymethyl-2,4,9-trithiaadamantane to produces 7-carbonyl-2,4,9-trithiaadamantane; and (3) reacting 7-carbonyl-2,4,9-trithiaadamantane with Ohira-Bestmann reagent to produces 7-ethynyl-2,4,9-trithiaadamantane. Molecular wires having 2,4,9-trithiaadamantane surface anchors are also disclosed.

14 Claims, 12 Drawing Sheets

7-ETHYNYL-2,4,9-TRITHIAADAMANTANE AND RELATED METHODS

This application claims priority of U.S. Provisional Patent Application Ser. No. 60/484,119, which is herein incorporated by reference in its entirety.

The U.S. Government has a paid-up license in this invention and the right in limited circumstances to require the patent owner to license others on reasonable terms as provided for by the terms of Grant No. DMR0210508 awarded by the National Science Foundation, and Grant No. DK61316-01 awarded by the National Institute of Health.

TECHNICAL FIELD

This invention relates to 7-ethynyl-2,4,9-trithiaadamantane, a method for its manufacture, and molecular wires having at least one trithiaadamantane surface anchor.

BACKGROUND OF THE INVENTION

In molecular-electronics manufacturing, there is a long-standing need to integrate or "anchor" a molecular wire into electronic circuitry. Molecular wires are substances or compounds that can transmit a signal between two points in a circuit. The signal is usually electronic, but it can be mechanical, optical, or even magnetic. And when the signal is electronic, the wires are often described as organic molecules with conjugated electronic systems that can effectively transmit electrons one dimensionally.

A molecular wire has one or more chemical functionalities that can bond to a metallic surface- and this is what secures the wire to a surface. These chemical functionalities are commonly referred to as surface anchors. Anchors also act as the wire-electrode interface. So it's important that the anchor provide a stable interface that facilitates the transmission of a signal.

A molecular wire becomes a molecular device when it bonds, via a surface anchor, to at least one electrode of an electronic circuit. A diode is such a molecular device. Molecular devices are used to control current characteristics or quantum effects on current-voltage behavior.

Many conventional surface anchors have a single sulfur atom that chemically bonds with a subject metallic surface, i.e., surfaces of electronic circuitry. So when these types of sulfur-based anchors are employed, the target substrate is typically coated with a thin gold film because a relatively strong bond forms between sulfur and gold. And although single sulphur-metal bonds do form, prior-art anchors based on single thiols or thioethers are inadequate because of: (1) the chemical instability that results from only a single bond with a target substrate and (2) the resulting surface orientation is unpredictable. More specifically regarding surface orientation, anchors that form only a single sulfur-metal bond with a metallic surface have a surface orientation that is often uncontrollable and unpredictable. For example, such an anchor's surface orientation could be either substantially vertical or substantially parallel to a metallic-film surface. Unpredictable surface orientation is problematic because it directly impacts the spatial orientation of the entire molecular wire.

The art can therefore be improved by providing anchors with improved stability and more predictable surface orientation compared to prior-art single-sulfur anchors. More specifically, the art can be improved with anchors that form multiple sulfur-metal bonds.

SUMMARY OF THE INVENTION

This invention provides a compound having the formula:

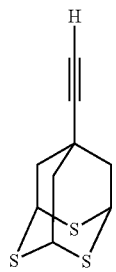

This invention further provides a method for manufacturing 7-ethynyl-2,4,9-trithiaadamantane comprising the step of: reacting 7-carbonyl-2,4,9-trithiaadamantane with Ohira-Bestmann reagent to produce 7-ethynyl-2,4,9-trithiaadamantane.

Also provided is a molecular wire having the formula:

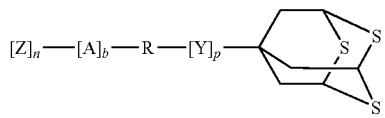

wherein A and Y are independently selected chemical functionalities;
wherein p is 0 or 1;
wherein b is 0 or an integer greater than or equal to 1;
wherein R is a compound that is capable of transferring a signal;
wherein Z is a surface anchor; and
wherein n is 0 or an integer greater than or equal to 1.

Also provided is a method for manufacturing a molecular wire comprising the step of chemically bonding, either directly or indirectly, trithiaadamantane to a compound that is capable of transferring a signal.

Also provided is a method for manufacturing 7-ethynyl-2,4,9-trithiaadamantane comprising the step of: reducing an alkyl 2,4,9-trithiaadamantane-7-carboxylate to produce 7-hydroxymethyl-2,4,9-trithiaadamantane; and oxidizing 7-hydroxymethyl-2,4,9-trithiaadamantane to produce 7-carbonyl-2,4,9-trithiaadamantane.

DETAILED DESCRIPTION OF THE ILLUSTRATIVE EMBODIMENTS

Figure 1:
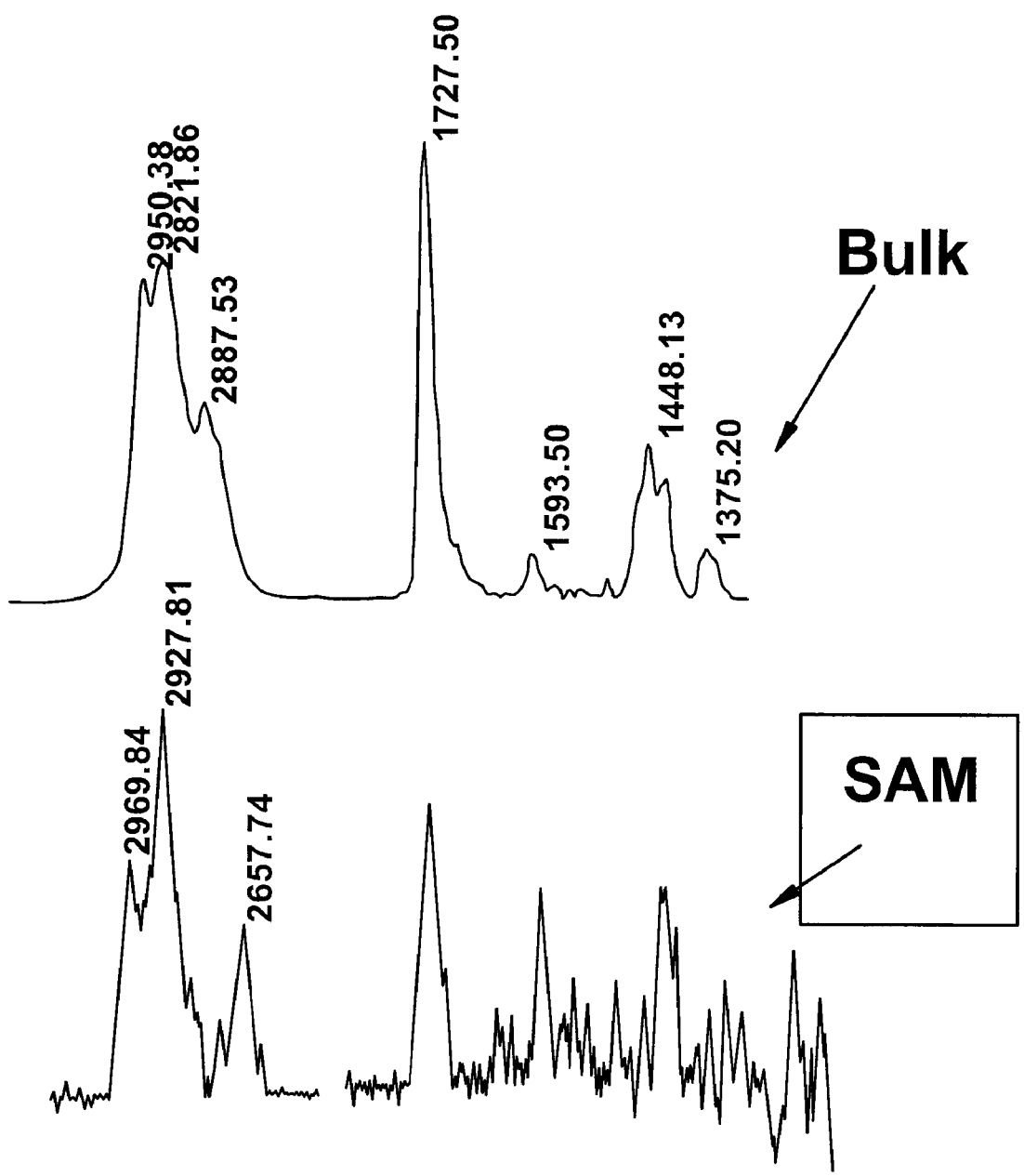
FIG. 1 is a polarization modulation FT-IR reflectance absorption of a self-assembled monolayer of 7-ethynyl-2,4,9-trithiaadamantane on a thin gold film.

This invention is generally directed to 7-ethynyl-2,4,9-trithiaadamantane, a method for its manufacture, and molecular wires having at least one trithiaadamantane surface anchor.

7-ethynyl-2,4,9-trithiaadamantane is represented by the formula:

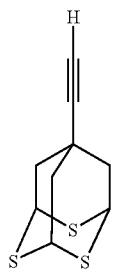

7-ethynyl-2,4,9-trithiaadamantane can be manufactured in three steps. First, an alkyl 2,4,9-trithiaadamantane-7-carboxylate is reduced to produce 7-hydroxymethyl-2,4,9-trithiaadamantane. Second, 7-hydroxymethyl-2,4,9-trithiaadamantane is oxidized to produce 7-carbonyl-2,4,9-trithiaadamantane. Third, 7-carbonyl-2,4,9-trithiaadamantane is reacted with Ohira-Bestmann reagent to produce 7-ethynyl-2,4,9-trithiaadamantane.

The method for manufacturing 7-ethynyl-2,4,9-trithiaadamantane is represented by the simplified reaction scheme:

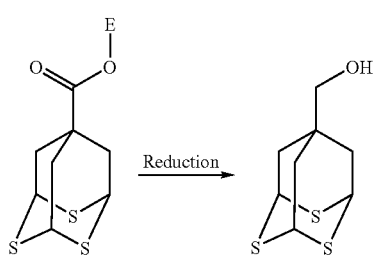

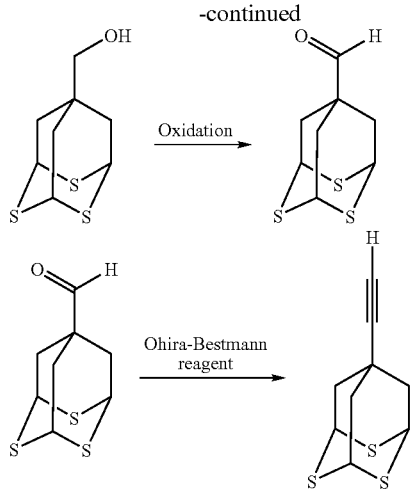

wherein E is an alkyl.

Method

First Step

In performing the first step, an alkyl 2,4,9-trithiaadamantane-7-carboxylate is reduced to produce 7-hydroxymethyl-2,4,9-trithiaadamantane. There are no limitations on the type of alkyl group that can be employed in the reaction, but a methyl group is preferred.

Alkyl 2,4,9-trithiaadamantane-7-carboxylate can be synthesized by reacting an oxidized alkyl triallyl acetate with a sulphuring agent and a Lewis acid. A general understanding of which can be gained from the following simplified reaction scheme:

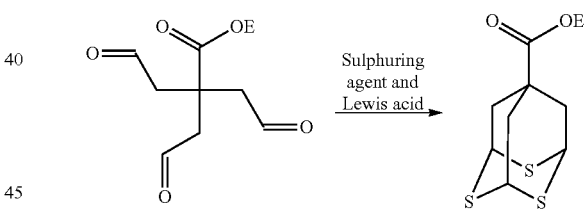

wherein E is an alkyl.

Oxidized alkyl triallyl acetate is manufactured by simply oxidizing an alkyl triallyl acetate. Any method of oxidation can be employed, but ozonolysis is preferred. An example of oxidizing methyl triallyl acetate via ozonolysis uses a solution of methyl triallyl acetate in freshly-distilled methylenechloride followed by stirring and cooling the solution to −78° C. in a dry-ice acetone bath. Ozone is subsequently bubbled through the cooled solution until a light-blue color persists. This method for oxidation is generally represented

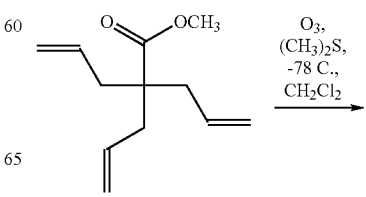

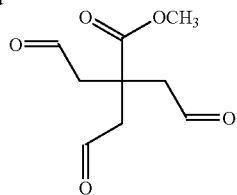

by the reaction scheme:

Any useful sulphuring agent can be employed in synthesizing an alkyl 2,4,9-trithiaadamantane-7-carboxylate. A sulfuring agent converts ketonic groups into thioketonic groups as represented by the reaction scheme:

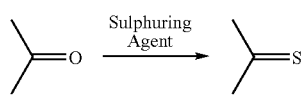

Preferred sulphuring agents include 1,3,2,4-dithiadiphosphetane-2,4-disulfide (Lawesson's reagent), phosphorous pentasulfide hexamethyldisiloxane (PPHD), or combinations thereof The relative mole ratio of sulphuring agent to oxidized alkyl triallyl acetate can generally range from about 6:1 to about 1:1. Preferably, the mole ratio ranges from about 3:1 to about 2:1.

Any Lewis acid can be employed in synthesizing an alkyl 2,4,9-trithiaadamantane-7-carboxylate. Preferred Lewis acids include the complex of boron trifluoride and ethyl ether ($BF_3.Et_2O$), the complex of boron trichloride and ethyl ether ($BCl_3.Et_2O$), or combinations thereof.

The mole ratio of Lewis acid to oxidized alkyl triallyl acetate preferably ranges from about 4:1 to about 1:1. More preferably, the mole ratio ranges from about 3:1 to about 2:1. Generally, the concentration of Lewis acid in the reaction medium ranges from about 0.5 to about 1.0 molar (M).

In synthesizing an alkyl 2,4,9-trithiaadamantane-7-carboxylate, any noncoordinated or weakly coordinated reaction solvent can be employed. Nonlimiting examples of preferred solvents are methylene chloride ($CH_2Cl_2$), carbon tetrachloride ($CCl_4$), benzene, or combinations thereof. Effective amounts of noncoordinated or weakly coordinated solvent can be determined by a person of ordinary skill in the art without undue experimentation.

Synthesis of alkyl 2,4,9-trithiaadamantane-7-carboxylate preferably occurs under reflux, and a person of ordinary skill in the art can determine the temperatures required for reflux without undue experimentation.

Alkyl 2,4,9-trithiaadamantane-7-carboxylate can be reduced by any useful method. Preferably, alkyl 2,4,9-trithiaadamantane-7-carboxylate is initially reacted with a reducing agent followed by a subsequent reaction with a proton donor. Without being bound to theory, reaction between alkyl 2,4,9-trithiaadamantane-7-carboxylate and a reducing agent produces a salt, and the proton donor subsequently aids in disassociating the salt to produce 7-hydroxymethyl-2,4,9-trithiaadamantane.

Useful reducing agents are in no way limited. Preferred reducing agents include diisobutylaluminum hydride, sodium tetrahydridoborate, lithium aluminum hydride, or combinations thereof.

In a preferred embodiment for reducing alkyl 2,4,9-trithiaadamantane-7-carboxylate, the reducing agent is reacted with alkyl 2,4,9-trithiaadamantane-7-carboxylate in a relative mole ratio ranging from about 5:1 to about 1:1. Preferably, the relative mole ratio ranges from about 3:1 to about 1:1.

Any proton donor can be employed, and preferred proton donors include water, methanol, and ethanol. Relative to the alkyl 2,4,9-trithiaadamantane-7-carboxylate salt, an excess of proton donors are generally present in the reaction medium. Preferably, the proton donors are present at a relative mole ratio to alkyl 2,4,9-trithiaadamantane-7-carboxylate salt ranging from about 10:1 to about 1:1; more preferably from about 5:1 to about 1:1.

Reduction via the disclosed method is preferably conducted in a liquid reaction medium that is preferably an inert organic solvent. Useful inert organic solvents are not limited and include toluene, benzene, and combinations thereof.

And reduction preferably occurs at a temperature ranging from about −78 to about 35° C.; preferably at temperatures ranging from about −10 to about 5° C. More preferably, reduction occurs at about 0° C.

Second Step

The second step of the subject method oxidizes 7-hydroxymethyl-2,4,9-trithiaadamantane to produce 2,4,9-trithia-tricyclo[3.3.1.13,7]dec-7-carbaldehyde. Oxidation is not limited to a particular method, although Swern oxidation conditions are preferred. Swern oxidation conditions are well known and generally describe a combination of reaction conditions such as reagents, temperature, pressure, and reaction medium. Preferred Swern oxidation conditions include at least one of the following three combinations of reagents: (1) oxalyl chloride and dimethyl sulfoxide; (2) trifluoroacetic anhydride and dimethylsulfoxide; and (3) triethylamine and diisopropylamine.

The Swern oxidation reagents are preferably present in an excess mole ratio relative to the amount of 7-hydroxymethyl-2,4,9-trithiaadamantane. In one embodiment, the Swern oxidation reagents are reacted with 7-hydroxymethyl-2,4,9-trithiaadamantane in a relative mole ratio ranging from about 5:1 to about 1:1, and in another embodiment, the relative mole ratio ranges from about 3:1 to about 1:1.

Oxidation is preferably conducted in an inert liquid reaction medium. Chlorinated organic solvents such as methylenechloride, carbontetracholoride, chloroform, and combinations thereof are preferred.

Oxidizing 7-hydroxymethyl-2,4,9-trithiaadamantane to produce (7-carbonyl-2,4,9-trithiaadamantane is preferably conducted under Swern oxidation conditions wherein the temperature ranges from about −100 to about −50° C. Preferably, the reaction is performed at a temperature of about −75° C.

Third Step

The Ohira-Bestmann reagent is well known, and any form thereof can be employed in performing the third step of the subject method. A preferred Ohira-Bestmann reagent is at least one of $CH_3COC(N_2)P(O)(OCH_3)_2$ and $CH_3COC(N_2)P(O)(OCH_2CH_3)_2$ in combination with at least one of $K_2CO_3$ and $Na_2CO_3$. So an example of a preferred Ohira-Bestmann reagent is the combination of $CH_3COC(N_2)P(O)(OCH_3)_2$ and $K_2CO_3$ Generally, an excess of Ohira-Bestmann reagent is employed. Preferably, Ohira-Bestmann reagent is reacted with 7-carbonyl-2,4,9-trithiaadamantane in a relative mole ratio ranging from about 5:1 to about 1:1, and more preferably from about 3:1 to about 1:1.

The third-step reaction between Ohira-Bestmann reagent and 7-carbonyl-2,4,9-trithiaadamantane is not limited to any particular reaction medium. Preferably, the reaction medium is an alcoholic solvent, and more preferably the reaction medium is selected from the group consisting of methanol and ethanol.

The third-step reaction is preferably conducted at a temperature ranging from about 20 to about 40° C. More preferably, the reaction is conducted at a temperature of about 30° C.

The subject method advantageously produces 7-ethynyl-2,4,9-trithiaadamantane at a yield greater than 50%. Preferably, the yield is greater than 75%.

Molecular Wire

The subject molecular wires have at least one trithiaadamantane surface anchor. The anchors are attached, either directly or indirectly, to a chemical compound that is capable of transmitting an electronic, optical, mechanical, or other type of signal. Indirect attachment occurs where a chemical functionality links the anchor to the compound. Any chemical functionality can be employed for indirect attachment, and preferred chemical functionalities include ethynyl and carboxylate. Direct attachment occurs where the anchor bonds with the compound, i.e., no chemical functionality links the two together.

Useful molecular wires have the formula:

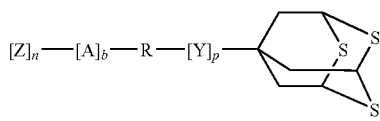

wherein A and Y are independently selected chemical functionalities;
wherein p is 0 or 1;
wherein b is 0 or an integer greater than or equal to 1;
wherein R is a moiety or functional group that is capable of transferring a signal;
wherein Z is a surface anchor; and
wherein n is 0 or an integer greater than or equal to 1.

When p is 0, trithiaadamantane is bonded directly to R. If b is 0 and n is an integer greater than or equal to 1, then R is bonded to directly to Z. Variables A and Y are preferably selected from ethynyl and carboxylate.

The molecular wires are preferably selected from the following:

[I]
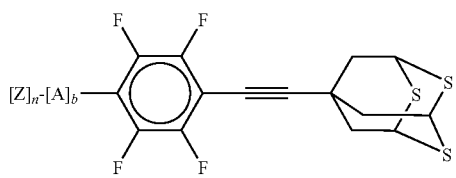

[II]
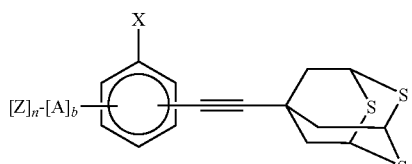

[III]
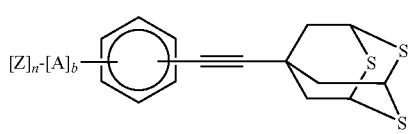

-continued

[IV]

[V]
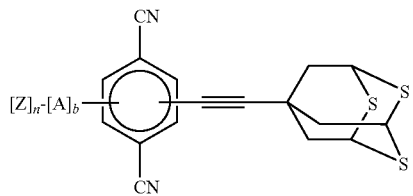

[VI]
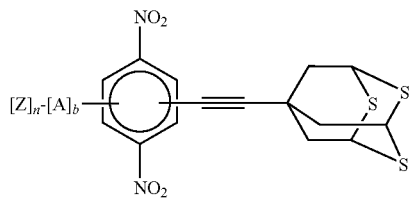

[VII]
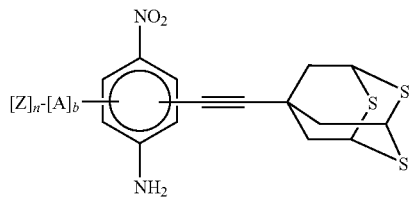

[VIII]
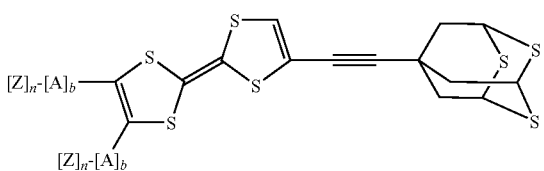

[IX]
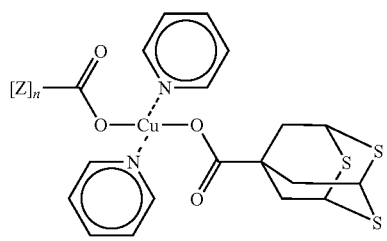

[X]
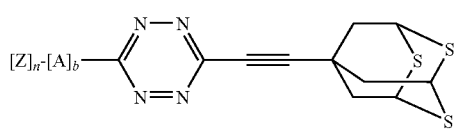

wherein M is a metallic element;

wherein X is a halogen; and wherein A, b, Z, and n are as described above.

Regarding the preferred molecular wires, trithiaadamantane, can bond, either directly or indirectly, with any available carbon atom on a cyclic organic compound- as indicated in the formulas by the loose position of the bond between trithiaadamantane and a cyclic compound. The same positional concept holds true for the variable Z, which is also depicted in the loose position.

The metallic element M, can be any metallic element, and it is preferably selected from platinum, palladium, or copper.

The halogen X is not limited to a specific halogen or group of halogens, but it is preferably fluorine, chlorine, bromine, or iodine.

The surface anchor Z can be any surface anchor, conventional or other, including trithiaadamantane. Nonlimiting examples of preferred surface anchors for the variable Z are:

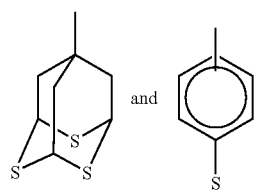

The subject molecular wires can be made by using conventional chemical methods. For example, 7-ethynyl-2,4,9-trithiaadamantane can be cross coupled with 4-sulfuracetylthioxy-iodobenzene by using the catalysts: CuI/diisopropylamine and Pd(PPh3)4. This synthesis is represented by the simplified reaction scheme:

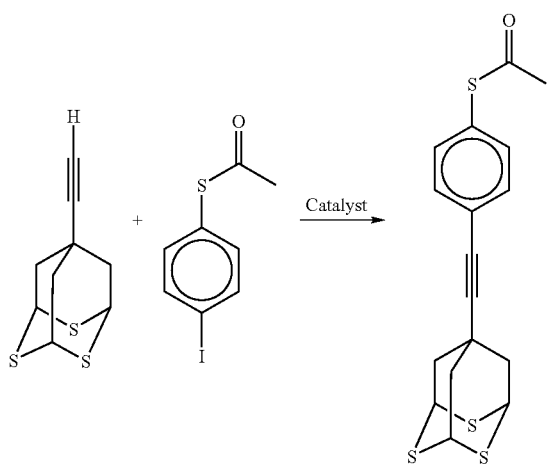

Reaction preferably occurs in an inert solvent such as dimethylformamide (DMF) and at a temperature ranging from about 75 to 150° C. More preferably, the reaction occurs under reflux for about two days.

An additional simplified reaction scheme for making a different embodiment of a molecular wire is presented:

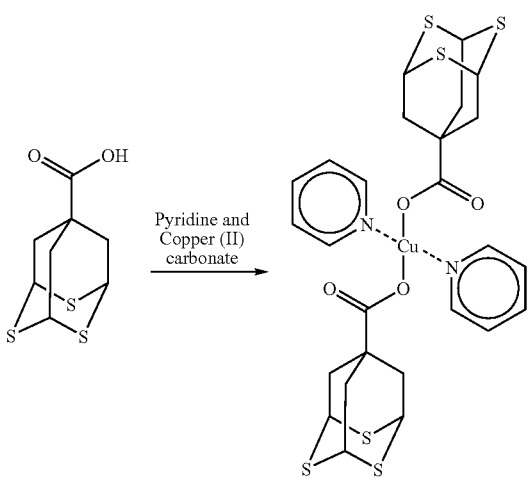

The above reaction preferably occurs in pyridine and at a temperature ranging from about 20 to 50° C. Preferably, the reaction occurs at room temperature for about two days.

2,4,9-trithiaadamantane-containing compositions can be used to form molecular wires that can span nanometer-sized junctions. The wires can be manually assembled or allowed to self assemble into a desired molecular device and bind to at least one of the device's metal surface, to form a well-defined interfacial structure. One embodiment of such a wire is based on the ligating 2,4,9-trithiaadamantane anchor, 2,4,9-trithiatricyclo(3.3.1.1)decane. To illustrate usage of a molecular wire according to the present invention, the use of the aforementioned molecular wire candidate to bridge two ruthenium metal clusters is described below, and its synthesis is illustrated in a reaction scheme. But, the scope of the present invention is not limited to any illustrative examples. The metal cluster complex described below represents merely one model of a junction that is promising for applications of electron transfer across a single molecule.

Without being bound or limited by theory, the trithiaadamantane tripod is a preferred anchor for constructing single molecular junctions for the following reasons: (1) the divalent sulfur atom is chemically more stable than thiolates under oxidative conditions and its metal binding capability is ensured by the chelating effect; (2) the rigid adamantane structure allows the construction of devices that are less susceptible to heat and temperature fluctuations; (3) the symmetrical shape and well-defined molecular geometry render the trithiaadamantane tripod promising for the formation of well-defined metal-molecule coordination interfaces that are suitable to be characterized and modeled; and (4) its compact structure should allow the formation of efficient junctions because the conductance for a coherent nonresonance junction increases exponentially as the distance between the metal contacts decreases.

It is recognized that 7-acetyl-2,4,9-trithiatricyclo(3.3.1.1) decane can be an intermediate for synthesizing molecular wire candidates, as illustrated in the following reaction scheme:

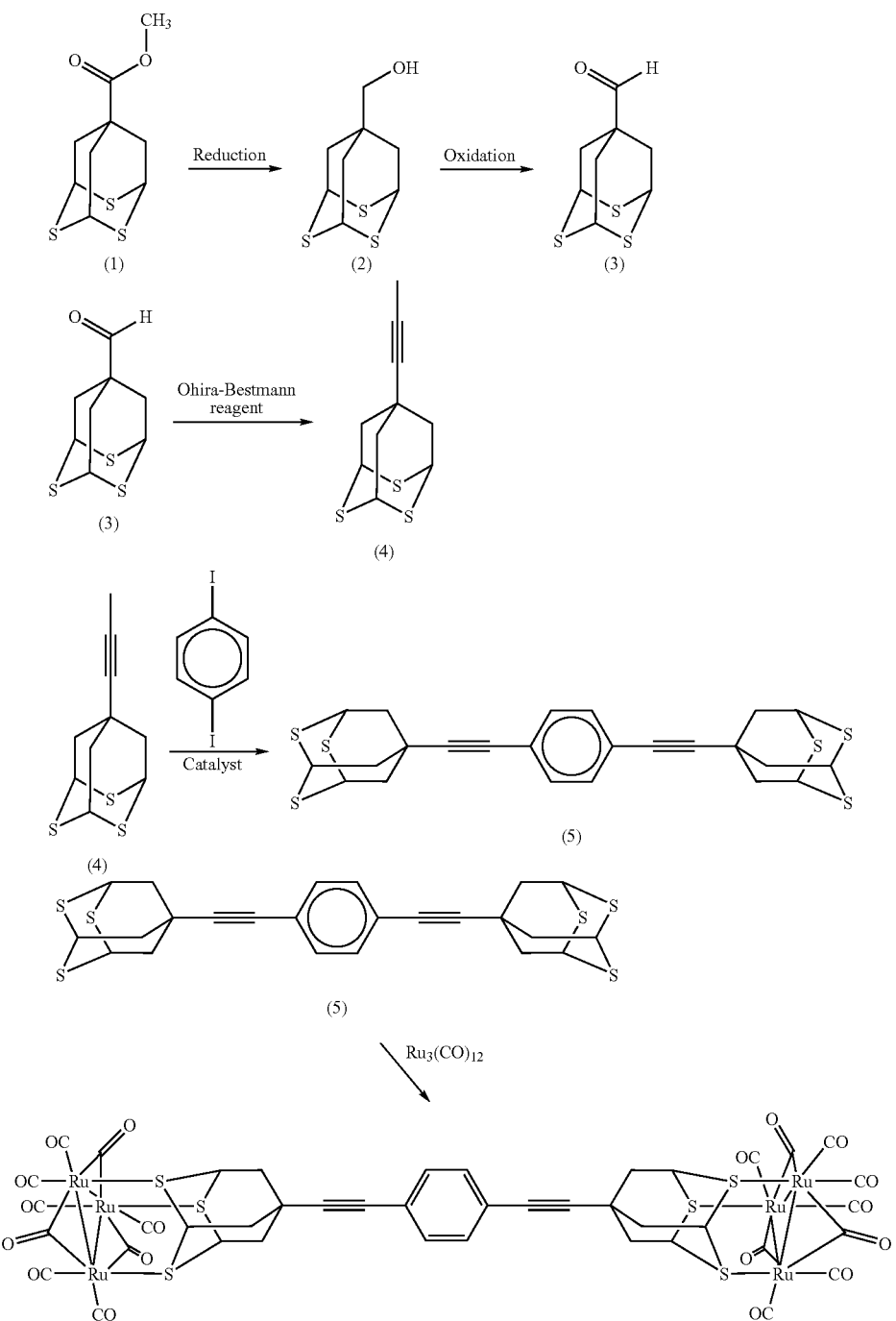

In the immediately preceding reaction scheme, an example of a suitable reducing agent is DIBAL-H; an example of a suitable oxidizing agent is $(CoCl)_2$/DMSO/TEA; an example of a suitable catalyst is $Pd(PPh_3)_4$ in a CuI/piperidine solution.

Insulation

Similar to conventional metallic wires used to transmit electrical energy to electronic devices, the molecular wire of the present invention can be provided with insulation to minimize the undesired conduction of electrical energy to surrounding features. The insulation can form a coating to at least partially enclose a molecular wire spanning a distance between two metallic surfaces. A preferred insulated molecular wire comprises an inclusion complex of 7-hydroxycarbonyl-2,4,9-trithiaadamantane in β-cyclodextrin.

Transition-metal ligands with $C_3$ symmetry have long been sought for uses in homogeneous catalysis and supramolecular coordination chemistry. The tridentate thioether ligand of 7-substituted 2,4,9-trithiaadamantane and its derivatives complex to several transition metals, transition metal clusters, and metal surfaces. Although it is possible to introduce chirality to the ligand by breaking the $C_{3v}$ symmetry through chemical modifications, the trithiaadamantane moiety forms an inclusion complex with a chiral host such as β-cyclodextrin. Other generally annular-shaped conical hosts can also form the chiral host of the present invention. The resulting guest-host complex is an asymmetric ligand in which the chiral host, β-cyclodextrin, provides a chiral cavity for binding, while the trithiaadamantane/metal complex moiety forms a catalytic active site when the guest is chemically cross-linked within the host.

β-Cyclodextrin is perhaps the best known natural host for small organic molecules. It is a cyclic oligosaccharide made of seven α-(1→4)-linked D-(+)-glucopyranose units. It has a generally annular conical shape with a hydrophilic exterior surface and a moderately non-polar internal cavity surface. The size of the internal cavity is suitable to accommodate the molecular wire, but preferred embodiments include an internal cavity that is about 0.8 nm long and about 0.7 nm in diameter, which provides a hydrophobic chiral environment for any small non-polar organic guest molecules. The driving force of inclusion complexes has traditionally been attributed to hydrophobic interactions, van der Waals-London dispersion forces and hydrogen bonding. Among the various known guest compounds of β-cyclodextrin, adamantane derivatives exhibit suitable binding stabilities, believed to be attributed to the close match of the structure of the adamantane framework to the inner cavity of β-cyclodextrin. This size match allows intimate van der Waals interactions between the guest and host molecules, because the intermolecular forces are highly distance dependent. One trithiaadamantane derivative, 7-hydroxycarbonyl-2,4,9-trithiaadamantane is described below as the guest molecule in an illustrative embodiment of an inclusion complex including β-cyclodextrin as the host material, 7-hydroxycarbonyl-2,4,9-trithiaadamantane differs from adamantane in that three carbon atoms in the 2, 4, and 9 positions of the adamantane carbon framework are substituted by sulfur atoms as follows:

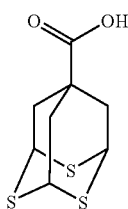

The substitutions produce two major structural perturbations in the adamantane framework: (1) the six membered ring containing the sulfur atoms is enlarged due to the larger van der Waals radii of sulfur than that of carbon; and (2) the compound becomes more polar because of the new C—S polar bonds. X-ray crystal structure and quantum mechanical calculations indicated that the structural perturbation results in a compatible size match between the 2,4,9-trithiaadamantane guest and the β-cyclodextrin host.

The formation of the inclusion complex was confirmed by $^1$H NMR, rotating-frame 2D nuclear Overhauser enhancement NMR spectroscopy ("ROSEY") and tandem mass spectrometry ("MS-MS"). The MS-MS and ROSEY-NMR data indicated that 7-hydroxycarbonyl-2,4,9-trithiaadamantane and β-cyclodextrin form an 1:1 inclusion complex. The ROSEY NMR experiments also showed that 7-hydroxycarbonyl-2,4,9-trithiaadamantane is oriented in the complex with the six-membered thioacetal end preferentially located at the larger opening of the β-cyclodextrin conical structure. An association constant of 1550 $M^{-1}$ was determined by $^1$H NMR titration for the complex at room temperature, which indicated 7-hydroxycarbonyl-2,4,9-trithiaadamantane to be one of many a suitable guests for a β-cyclodextrin host.

Figure 9:
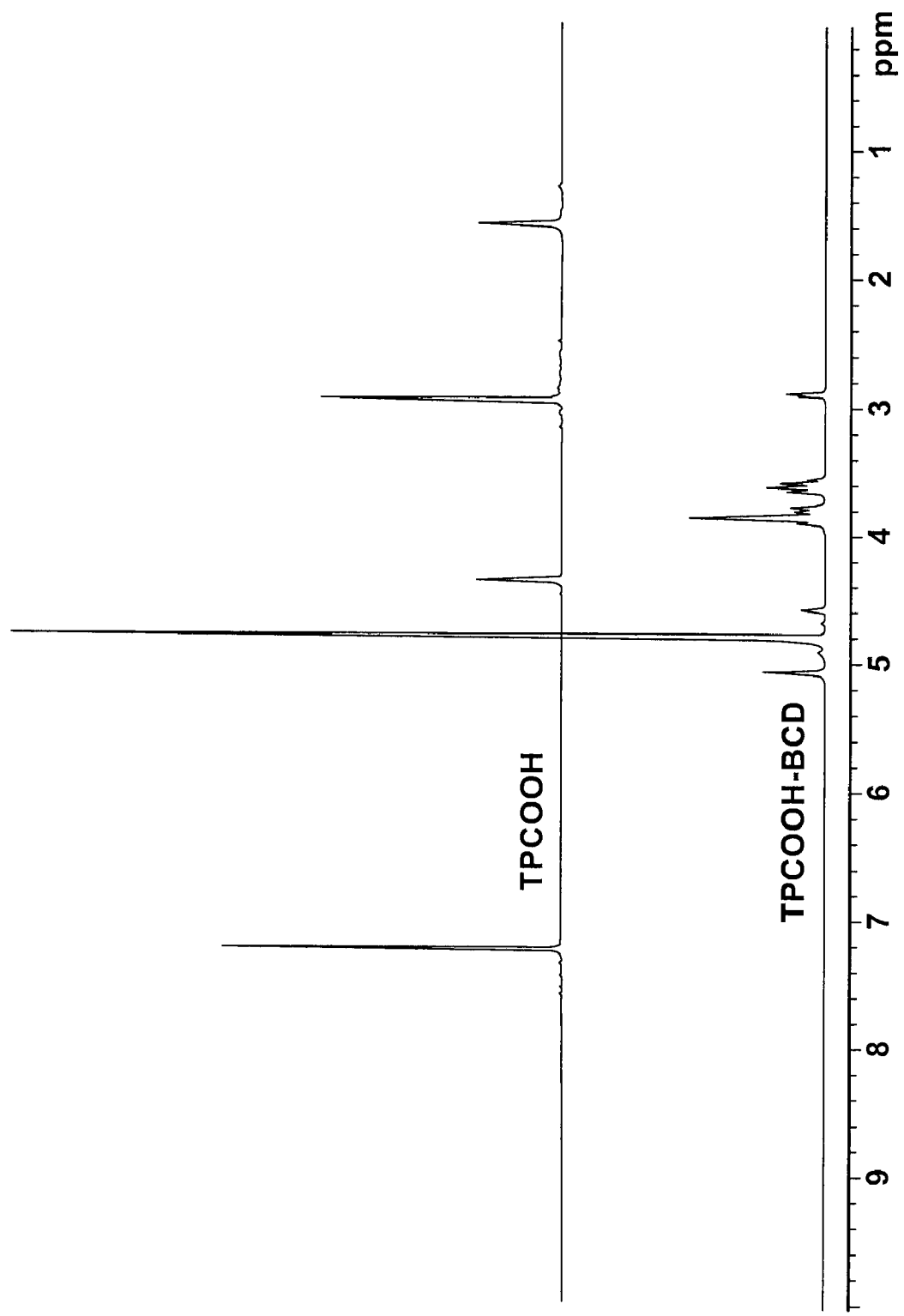
FIG. 9 is $^1$H NMR spectra of 7-hydroxycarbonyl-2,4,9-trithiaadamantane and 7-hydroxycarbonyl-2,4,9-trithiaadamantane/β-cyclodextrin inclusion complexes.

The formation of inclusion complex between 7-hydroxycarbonyl-2,4,9-trithiaadamantane and β-cyclodextrin was evident in the $^1$H NMR experiments. 7-hydroxycarbonyl-2,4,9-trithiaadamantane dissolves only slightly in water. When β-cyclodextrin was present in the solution, its solubility increased visibly. Thus, a 1:1 mixture of 7-hydroxycarbonyl-2,4,9-trithiaadamantane and β-cyclodextrin ($3.5 \times 10^{-3}$ M) formed a clear solution in $D_2O$ in an NMR sampling tube. At the low concentration limit, this change in the solubility of 7-hydroxycarbonyl-2,4,9-trithiaadamantane in water is attributed to the molecular interactions between water insoluble 7-hydroxycarbonyl-2,4,9-trithiaadamantane and water soluble β-cyclodextrin. The $^1$H NMR spectrum of the resulting solution showed significant changes in the chemical shifts of 7-hydroxycarbonyl-2,4,9-trithiaadamantane and β-cyclodextrin (FIG. 9). Similar phenomena in cyclodextrin inclusion complexes have been observed previously. Without being bound by theory, these spectral changes were attributed at least in part to the dynamic exchanges between uncomplexed species and the intimately included 7-hydroxycarbonyl-2,4,9-trithiaadamantane in β-cyclodextrin in aqueous solutions. It is worth noting that significant line broadening due to the complexation was not observed, indicating that the complexation equilibrium is at the fast exchange limit of the NMR time scale at room temperature. The simultaneous observation of changes in the chemical shift of the β-cyclodextrin at H-3 and H-5 also indicated the binding interaction was dominated by the inclusion of the 7-hydroxycarbonyl-2,4,9-trithiaadamantane guest inside the host β-cyclodextrin cavity.

Figure 10:
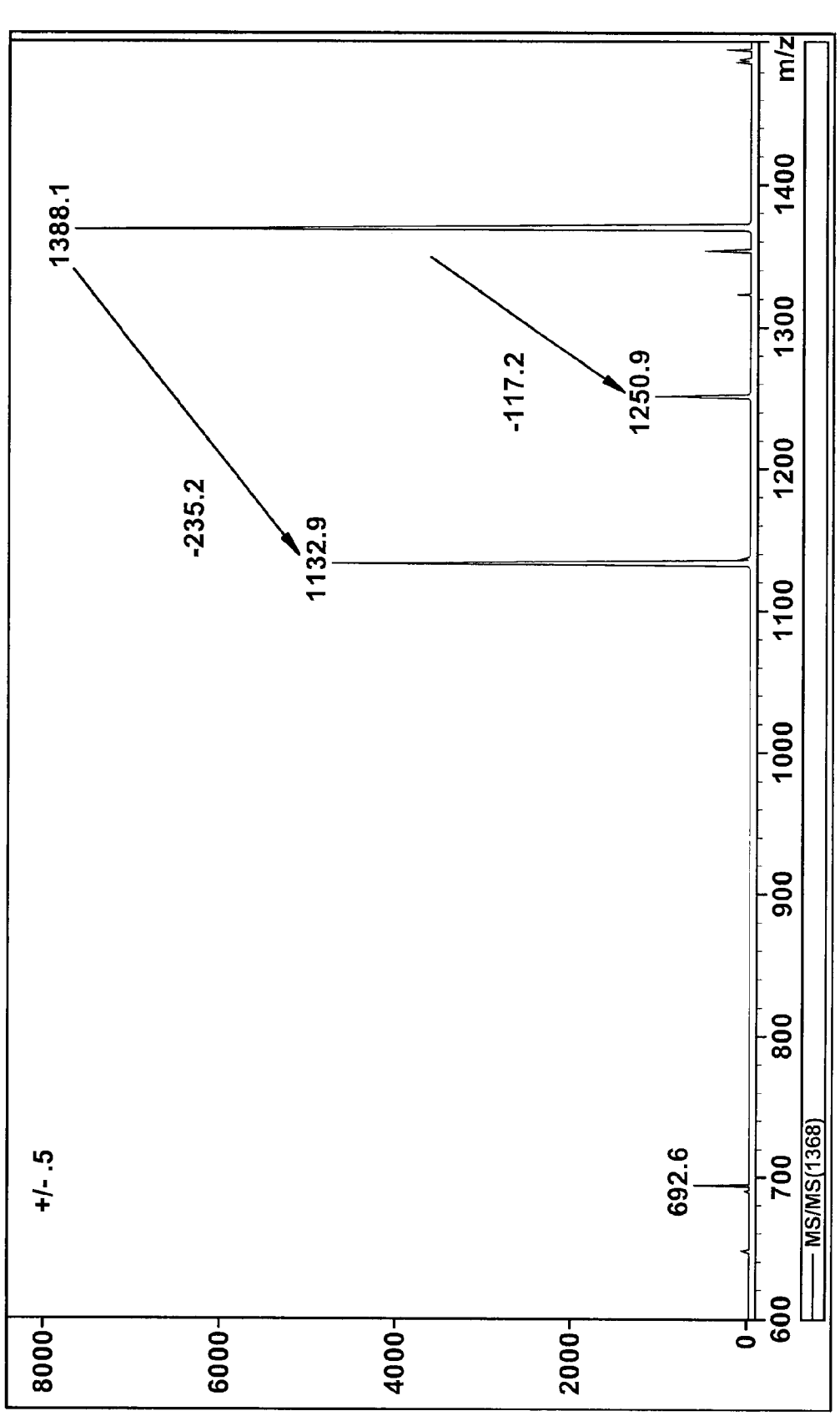
FIG. 10 is an electrospray MS/MS spectrum of the inclusion complex of 7-hydroxycarbonyl-2,4,9-trithiaadamantane and β-cyclodextrin.

The formation of the inclusion complex between 7-hydroxycarbonyl-2,4,9-trithiaadamantane and β-cyclodextrin was also investigated by electrospray tandem mass spectrometry. When a solution of 7-hydroxycarbonyl-2,4,9-trithiaadamantane and β-cyclodextrin in water was electrospray ionized, the corresponding 1:1 complex peak was observed (m/z=1368 D) in the negative ion mass spectrum. The nature of this ion was confirmed by collision activation of the mass selected ion at m/z=1368 D, which fragmented preferentially into the pseudo-molecular ion of β-cyclodextrin m/z=1133 in the MS/MS spectrum shown in FIG. 10.

The structure and the detailed guest-host interactions of the 7-hydroxycarbonyl-2,4,9-trithiaadamantane/β-cyclodextrin inclusion complex were further investigated with 2D ROSEY NMR spectroscopy. Intermolecular Nuclear Overhauser Effect NMR spectroscopy (NOEs) provides three-space spin-interaction information, and thus, has been widely used for 3D structural characterization of supramolecular complexes. However, β-cyclodextrin, which has a molecular mass of about 1400 Da, falls into a small cross relaxation-rate regime due to its unfavorable tumbling rate in $D_2O$. Rotating frame NOE (ROSEY) pulse sequence overcomes this limitation by application of an additional excitation pulse which allows observation of the transverse magnetization enhancement from cross relaxation, and is thus used for characterizing the inclusion complex in our study. Strong NOE correlation peaks were observed in the ROSEY experiments, which correlates the $H_b$ protons of the 7-hydroxycarbonyl-2,4,9-trithiaadamantane in the close space proximity with the H-5 protons of the β-cyclodextrin and $H_a$ protons with H-3 proton.

Figure 11:
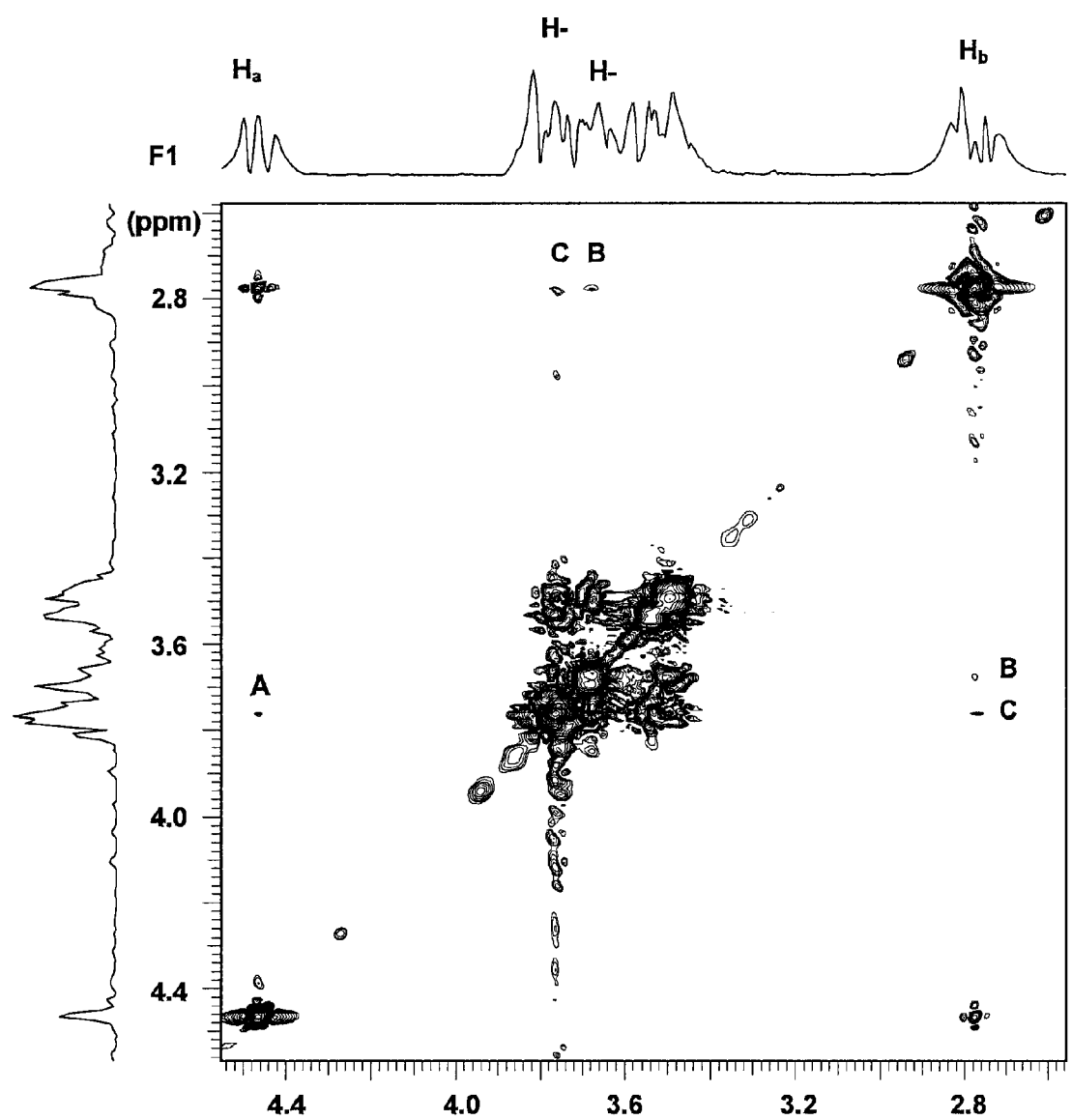
FIG. 11 is a 2D ROSEY spectrum of 7-hydroxycarbonyl-2,4,9-trithiaadamantane and β-cyclodextrin inclusion complex.

The 2D ROSEY spectrum of TPCOOH and β-cyclodextrin inclusion complex can be found in FIG. 11. The location of the 7-hydroxycarbonyl-2,4,9-trithiaadamantane in the β-cyclodextrin is thus illustrated in Scheme 1 with the carboxylic-acid end group of the 7-hydroxycarbonyl-2,4,9-trithiaadamantane included into the small end of the cavity and the thioacetal end located in the big rim of the cavity.

The equilibrium constant of the formation of the inclusion complex provides a relative measurement of the thermodynamic driving force for the guest and host binding. NMR Titration was performed by measuring chemical shift changes as a function of the relative concentrations of the host and guest. The changes of the chemical shifts were measured for the H-3 and H-5 peaks of the host and $H_a$ and $H_b$ of the guest in the following scheme, which represents the inclusion complex formation of 7-hydroxycarbonyl-2,4,9-trithiaadamantane with β-cyclodextrin:

Scheme 1

Figure 12:
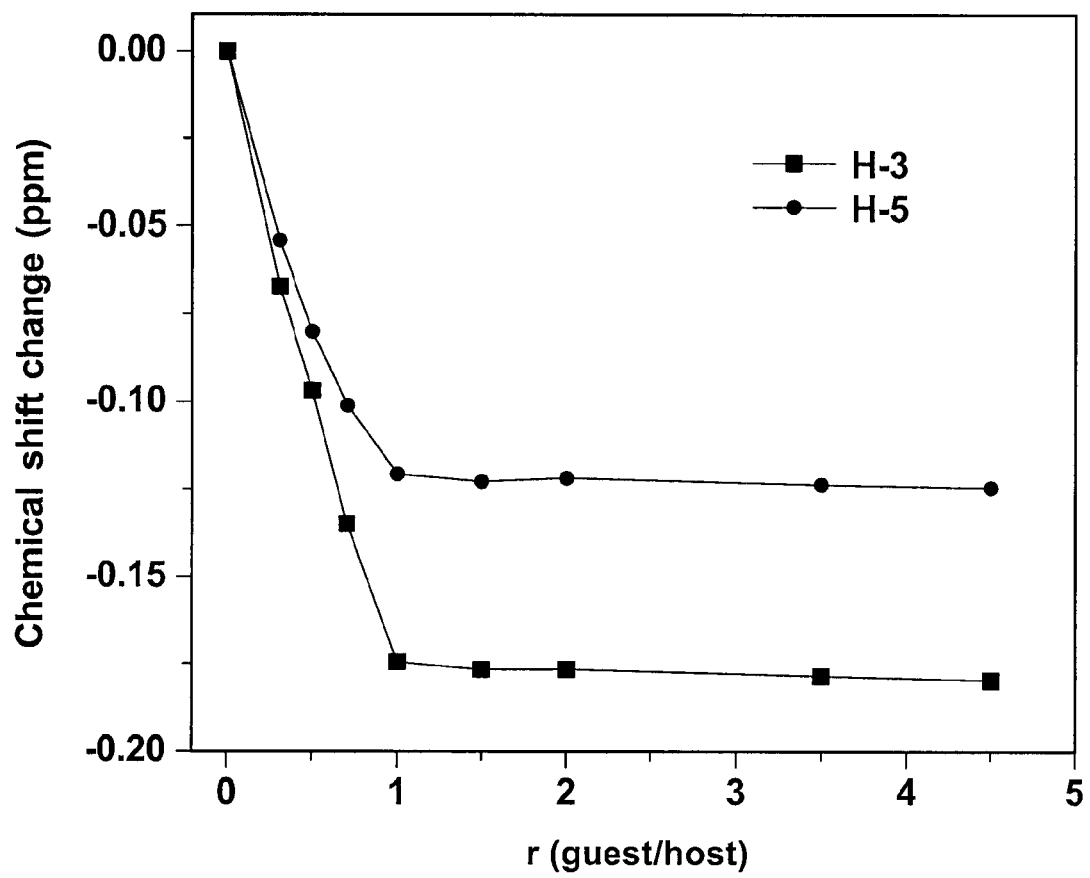
FIG. 12 illustrates the chemical shift changes for H-3 and H-5 protons of the inclusion complex of 7-hydroxycarbonyl-2,4,9-trithiaadamantane and β-cyclodextrin at different guest-host molar ratios.

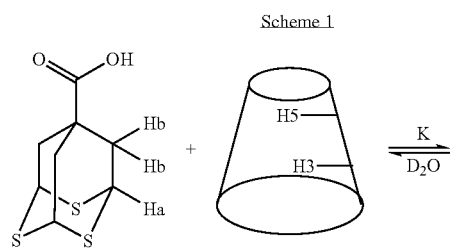

of the host as the internal reference. Plotting $\Delta\delta$ against the guest/host ratio (r) for the host protons as shown in FIG. 12, two lines with steep slopes and leveling off at r=1 were obtained, indicating the complex to be 1:1 for 7-hydroxycarbonyl-2,4,9-trithiaadamantane and β-cyclodextrin.

The data in Table 1 were also used to calculate the stability constant of the 7-hydroxycarbonyl-2,4,9-trithiaadamantane/β-cyclodextrin inclusion complex by applying the Benesi-Hildebrand equation having the formula:

$$1/\Delta\delta_i = (1/K\Delta\delta_c)(1/H_i) + 1/\Delta\delta_c$$

where the $\Delta\delta_i$ represents the observed chemical shift difference between the free guest and complexed guest, $H_i$ represents the total host concentration, and $\Delta\delta_c$ represents the guest chemical shift difference between a completely complexed state and completely free state. In order to use Benesi-Hildebrand equation, the host molecule must be present in excess. The stability constant was determined from simultaneous fits of three chemical shift data sets. The stability constant of 7-hydroxycarbonyl-2,4,9-trithiaadamantane/β-cyclodextrin in water was thus measured to be 1550·M$^{-1}$ (log K=3.19). It was found that the stability constant for 7-hydroxycarbonyl-2,4,9-trithiaadamantane is significantly higher than that of 1-adamantanecarboxylic acid/β-cyclodextrin inclusion complex (K=188 M$^{-1}$), indicating that 7-hydroxycarbonyl-2,4,9-trithiaadamantane is a suitable guest molecule for the β-cyclodextrin host.

TABLE 1

$^1$H NMR chemical shifts and displacements of the inclusion complex of TPCOOH and β-cyclodextrin

| | Entry | | | | | | | | |
|---|---|---|---|---|---|---|---|---|---|
| | 1 | 2 | 3 | 4 | 5 | 6 | 7 | 8 | 9 |
| Ratio$_{(TPCOOH/\beta-CD)}$ | 0 | 0.3 | 0.5 | 0.7 | 1.0 | 1.5 | 2.0 | 3.5 | 4.5 |
| $\delta_{H3\,(ppm)}$ | 3.978 | 3.911 | 3.881 | 3.843 | 3.803 | 3.801 | 3.801 | 3.799 | 3.798 |
| $\delta_{H5\,(ppm)}$ | 3.891 | 3.837 | 3.811 | 3.790 | 3.770 | 3.768 | 3.769 | 3.767 | 3.766 |
| $\delta_{Ha\,(ppm)}$ | 4.355 | 4.596 | 4.594 | 4.592 | 4.583 | 4.580 | 4.579 | 4.580 | 4.575 |
| $\delta_{Hb\,(ppm)}$ | 2.950 | 2.898 | 2.903 | 2.897 | 2.894 | 2.895 | 2.894 | 2.894 | 2.889 |
| $\Delta\delta_{H3\,(ppm)}$ | 0.000 | −0.067 | −0.097 | −0.135 | −0.175 | −0.177 | −0.177 | −0.179 | −0.180 |
| $\Delta\delta_{H5\,(ppm)}$ | 0.000 | −0.054 | −0.080 | −0.101 | −0.121 | −0.123 | −0.122 | −0.124 | −0.125 |
| $\Delta\delta_{Ha\,(ppm)}$ | 0.000 | 0.241 | 0.239 | 0.237 | 0.228 | 0.225 | 0.224 | 0.225 | 0.220 |
| $\Delta\delta_{Hb\,(ppm)}$ | 0.000 | −0.052 | −0.047 | −0.053 | −0.056 | −0.055 | −0.056 | −0.056 | −0.061 |

-continued

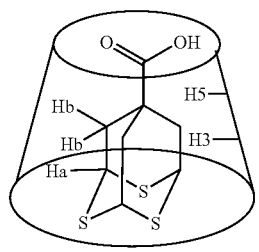

As shown in Table 1, the formation of inclusion complex induces upfield shifts for both the H-3 and H-5 protons on the β-cyclodextrin. The protons of 7-hydroxycarbonyl-2,4,9-trithiaadamantane shifted down field. The stoichiometry of the complex was calculated by using the anomeric proton H-1

Insulation Experimental

Materials

β-Cyclodextrin was used as received. 7-hydroxycarbonyl-2,4,9-trithiaadamantane was prepared by base hydrolysis of 7-ethoxycarbonyl-2,4,9-trithiaadamantane, which was prepared according to the method set forth in Kittredge, K. W.; Minton, M. A.; Fox, M. A.; Whitesell, J. K. *Helvetica Chimica Acta* 2002, 85, 788, which is incorporated in its entirety herein by reference. Specifically, to a solution of ethyl triallyl acetate (2.85 g, 13.70 mmol) in freshly distilled CH$_2$Cl$_2$ (100 mL) in a 250 mL three-neck flask was bubbled through O$_3$ generated in situ with an OREC ozone generator (Ozone Research and Equipment Inc.) at −78° C. The reaction was allowed to continue while stirring until the reaction mixture displayed a light blue color. The ozone line then was replaced by an argon line to flush the reaction mixture for 10 min. After addition of (CH$_3$)$_2$S (3.5 mL, 41.10 mmol), the reaction mixture was allowed to warm up slowly from −78° C. to the ambient temperature and then transferred to a 250-mL round bottom flask. After removing the solvent by a rotary evaporator and subsequently a mechanical pump at the ambient temperature, the resulting yellow viscous residue was re-dissolved in $CH_2Cl_2$ (100 mL). Lawesson's reagent (5.54 g, 13.7 mmol) and boron trifluoride etherate (5.80 mL, 41.10 mmol) were added respectively to the above solution which was then refluxed for 100 hours under argon. The reaction mixture was allowed to cool to the ambient temperature, washed with aqueous potassium carbonate (0.2 M, 3×15 mL), dried over anhydrous magnesium sulfate. A brownish oil residue was produced after filtration and evaporation of the solvent, which upon column chromatography furnished a white crystal (1.23 g, 38% yield). $^1H$ NMR ($CDCl_3$): δ 1.27 (3 H, $CH_3$, t, J=7.20 Hz), 2.89 (6 H, $CH_2$, d, J=3.00 Hz), 4.17 (2 H, $OCH_2$, q, J=7.20 Hz), 4.32 (3 H, broad, CH, s) ppm; $^{13}C$ NMR ($CDCl_3$): δ 14.29, 38.46, 40.06, 41.31, 61.33, 175.06 ppm; IR (ATR): 1050, 1104, 1180, 1213, 1272, 1493, 1724, 2922 $cm^{-1}$. HRMS: calcd for $C_{10}H_{12}O_2S_3Na^+$: 285.00536, found 285.00435.

The above 7-ethoxycarbonyl-2,4,9-trithiaadamantane product (175 mg, 0.66 mmol) was dissolved in a mixture of tetrahydrofuran:methanol:water (2 mL, 3:3:1) and was added $LiOH.H_2O$ (140 mg, 6.6 mmol) in a 10-mL pear-shaped flask connected to a reflux condenser. The reaction mixture was stirred at room temperature for 1 hour and refluxed for additional 15 minutes. The reaction mixture was allowed to cool to ambient temperature, diluted with water (2 mL), acidified to pH~2 with HCl (6 M), and allowed to complete the formation of a precipitate in a 5° C. refrigerator overnight. Filtration and high-vacuum drying overnight afforded a light yellow solid (140 mg, 90% yield). $^1H$ NMR (($CD_3$)$_2CO$): δ 2.82 (1 H, broad, OH, s), 2.88 (6 H, $CH_2$, d, J=3.30 Hz), 4.49 (3 H, broad, CH, s) ppm; $^{13}C$ NMR ($CDCl_3$): δ 202.11, 42.09, 39.41, 38.90 ppm. IR (ATR): 826, 930, 1006, 1042, 1103, 1184, 1228, 1277, 1300, 1421, 1445, 1694, 2920, 2933, 2290-3300 $cm^{-1}$.

$^1H$ NMR Study

NMR spectra were recorded with Varian Gemini-300 NMR spectrometer at 298 K. In the NMR titration measurements, the samples were prepared by varying the ratio of 7-hydroxycarbonyl-2,4,9-trithiaadamantane to β-cyclodextrin in $D_2O$ (1~10×$10^{-3}$ M). The NMR samples were allowed to thoroughly mix and equilibrate overnight in NMR tubes before the spectra were acquired. For the 2D-ROSEY experiments, a unity-750 NMR spectrometer was employed. The pulse sequence used in Bax, A.; Davis, D. G. *J. Magn. Reson.* 1985, 63, 207, incorporated in its entirety herein by reference, was applied and the optimum mixing time was found to be 500 ms.

Calculation of the Stability Constant K

The stability constant of the inclusion complex was calculated from $^1HNMR$ titration data using a non-linear least squared fit of the data to the Benesi-Hildebrand equation as described in Benesi, H. A.; Hildebrand, J. H. *J. Am. Chem. Soc.* 1949, 71, 2703, which is incorporated in its entirety by reference, employing the data analysis software Origin (Microcol™ software, Inc.).

EXAMPLES

In order to demonstrate the present invention, the following examples have been prepared and tested. The examples should not, however, be viewed as limiting the scope of the invention. The claims will serve to define the invention.

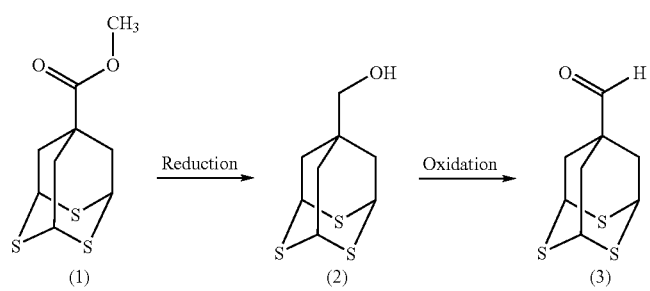

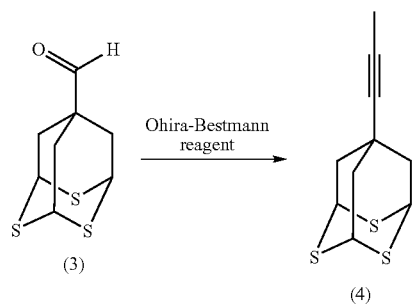

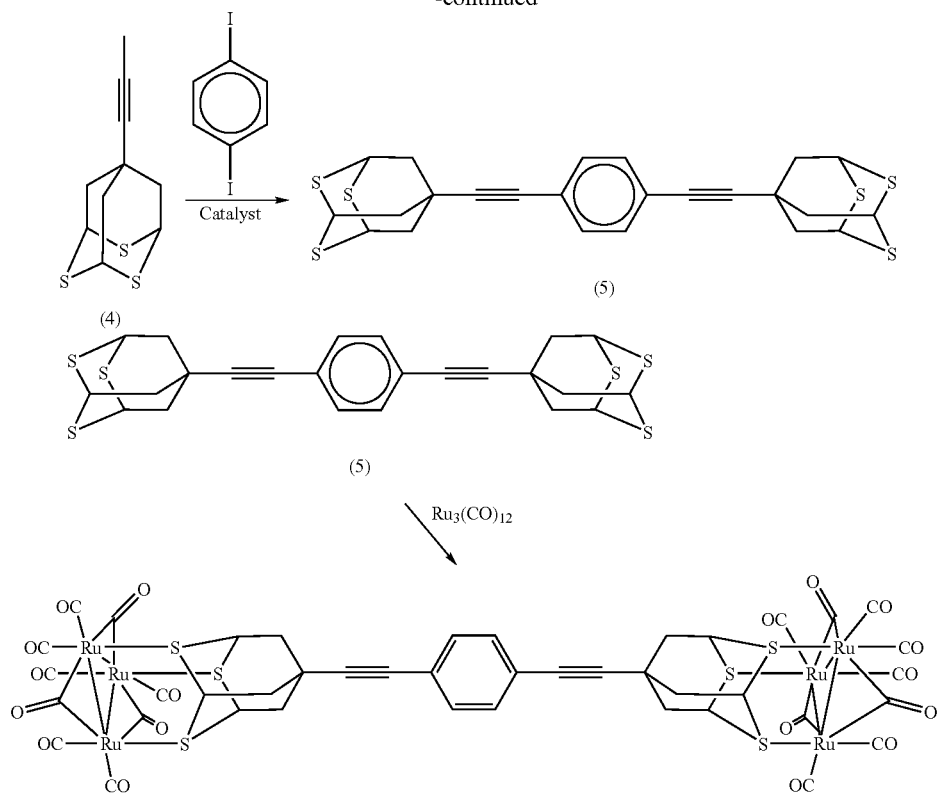

As shown above, Ester (1) was converted to aldehyde (3) by the sequential DIBAL reduction, and Swern oxidation. The Ohira-Bestmann reagent was found to be effective for converting aldehyde (3) to alkyne (4). Species (4) underwent facile Sonogashira cross-coupling with diiodobenzene to furnish the prototypical molecular wire candidate (5). This synthetic protocol is highly amenable to variation, and a variety of bridging units can be incorporated into the scheme to examine structural and electronic effects on the various molecular wire candidates.

Figure 2:
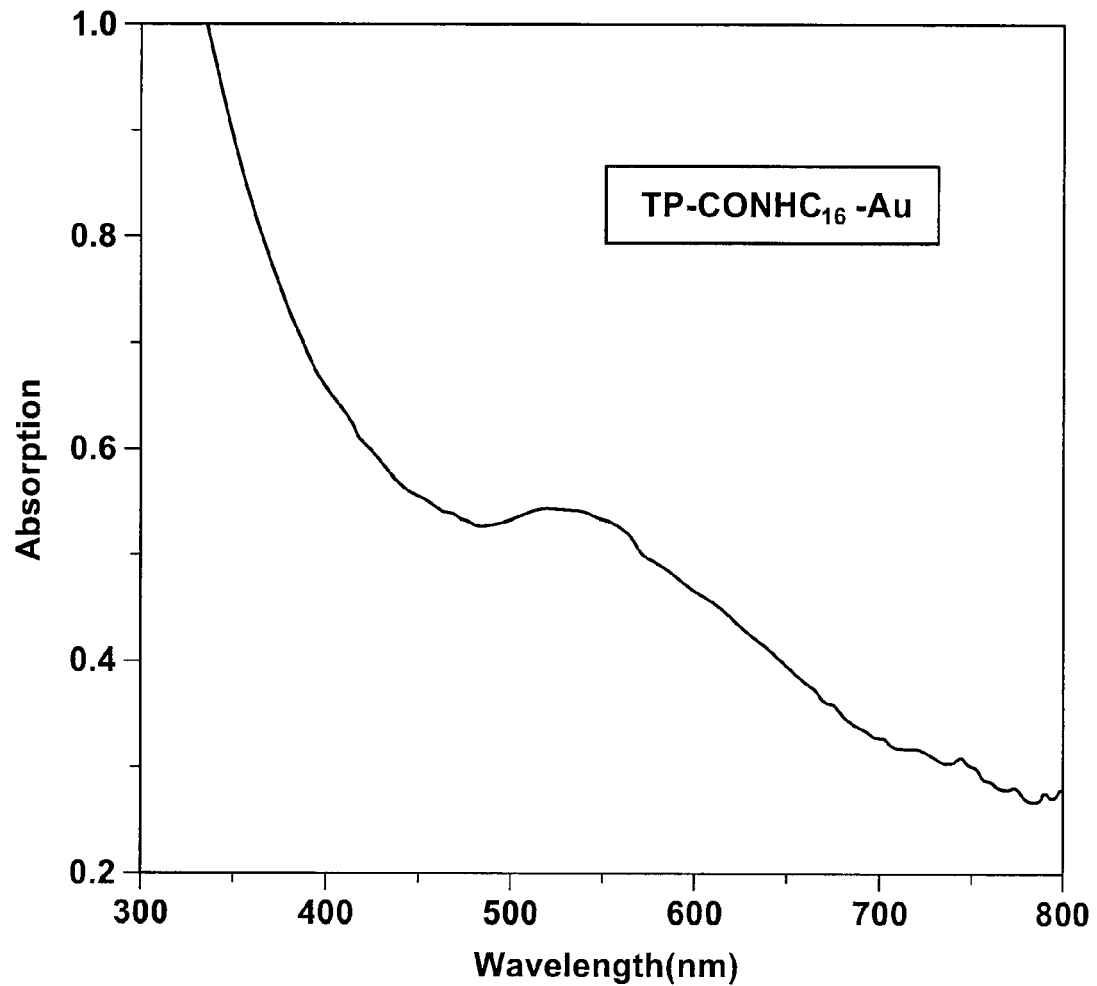
FIG. 2 is a self-assembled monolayer of 7-ethynyl-2,4,9-trithiaadamantane on colloidal gold nanoparticles observed by UV-vis Absorption.
Figure 3:
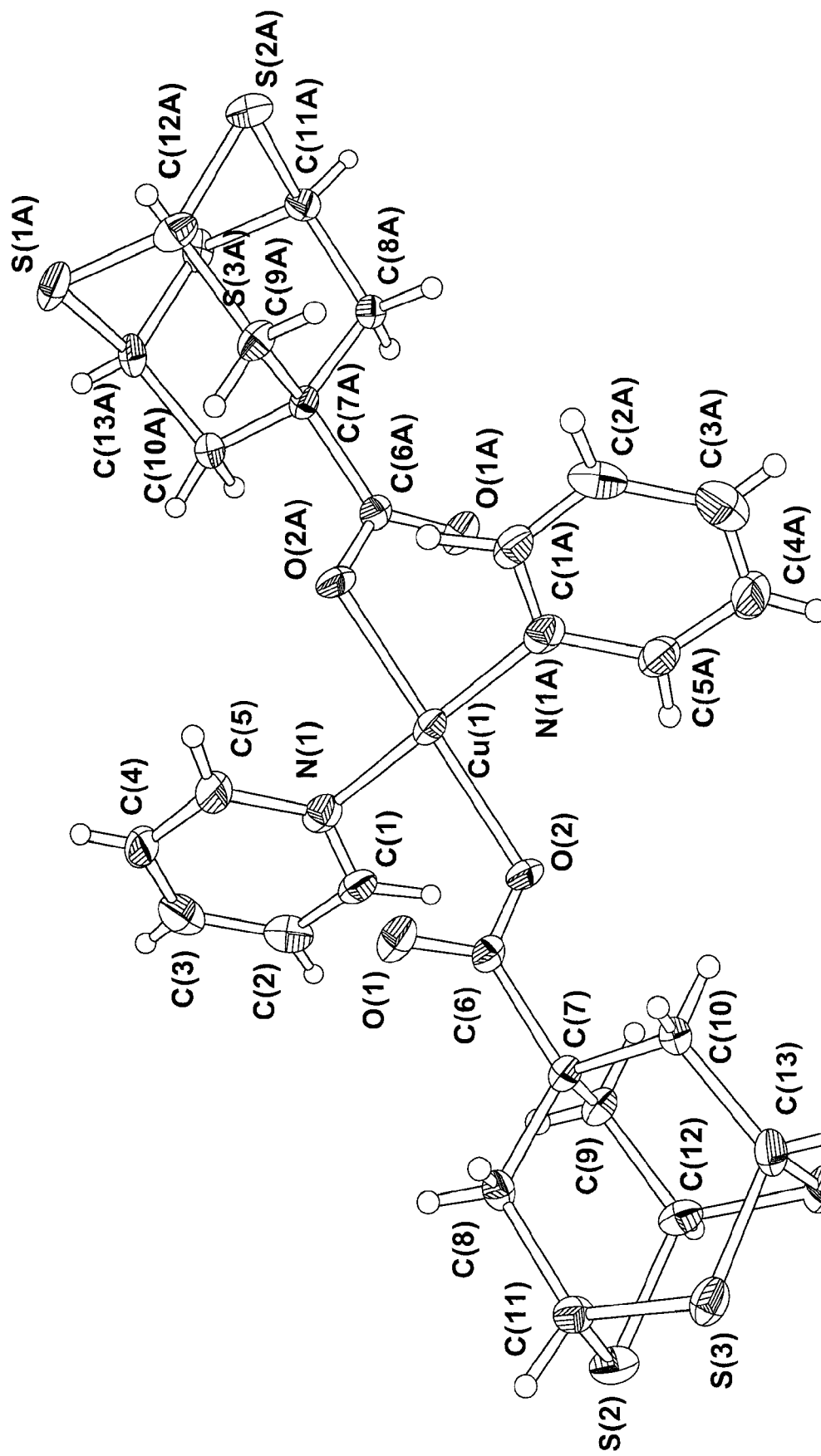
FIG. 3 is an X-ray crystal structure of a Cu(II)-linked molecular wire.
Figure 4:
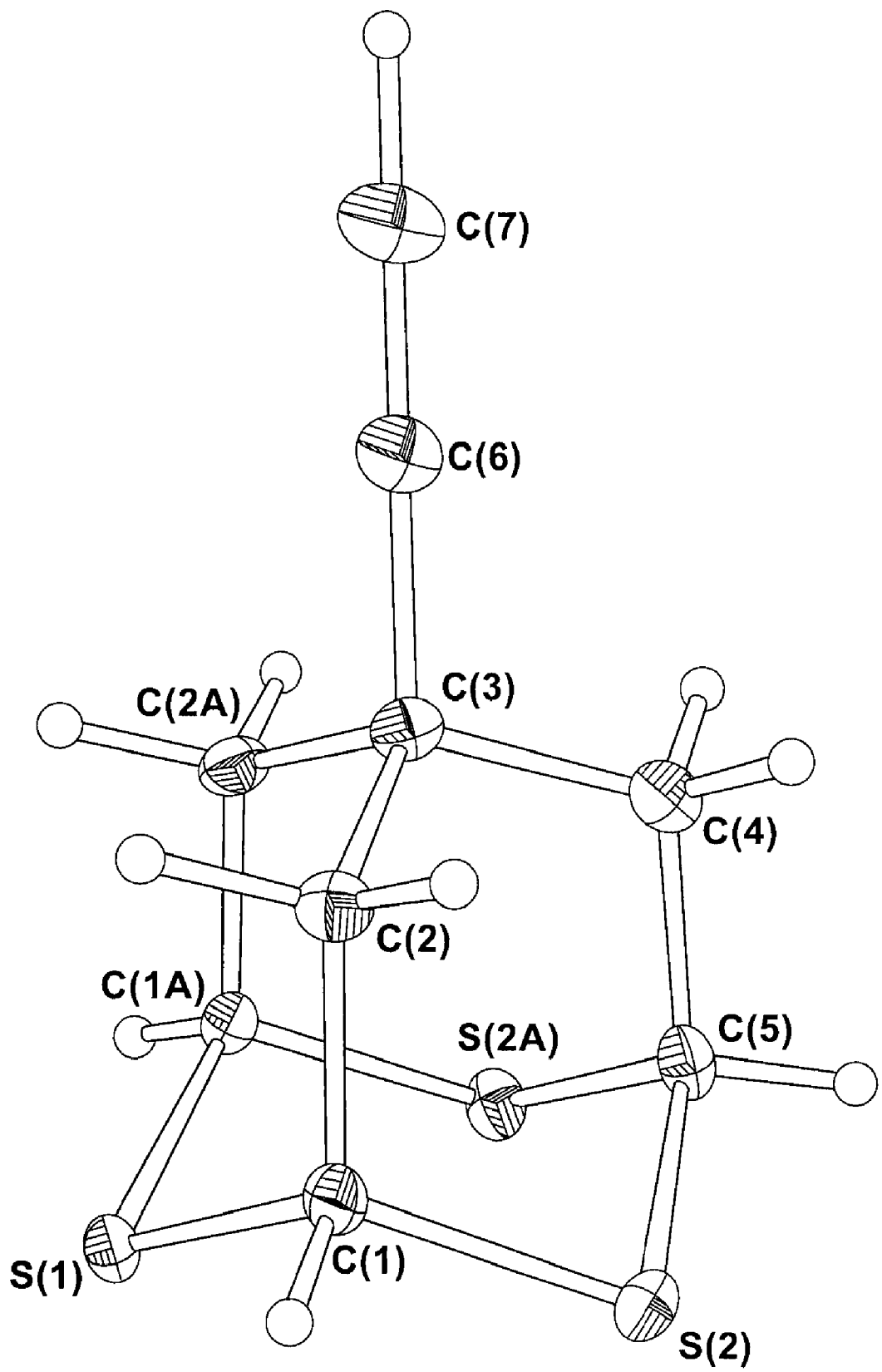
FIG. 4 is an X-ray crystal structure of 7-ethynyl-2,4,9-trithiaadamantane.
Figure 5:
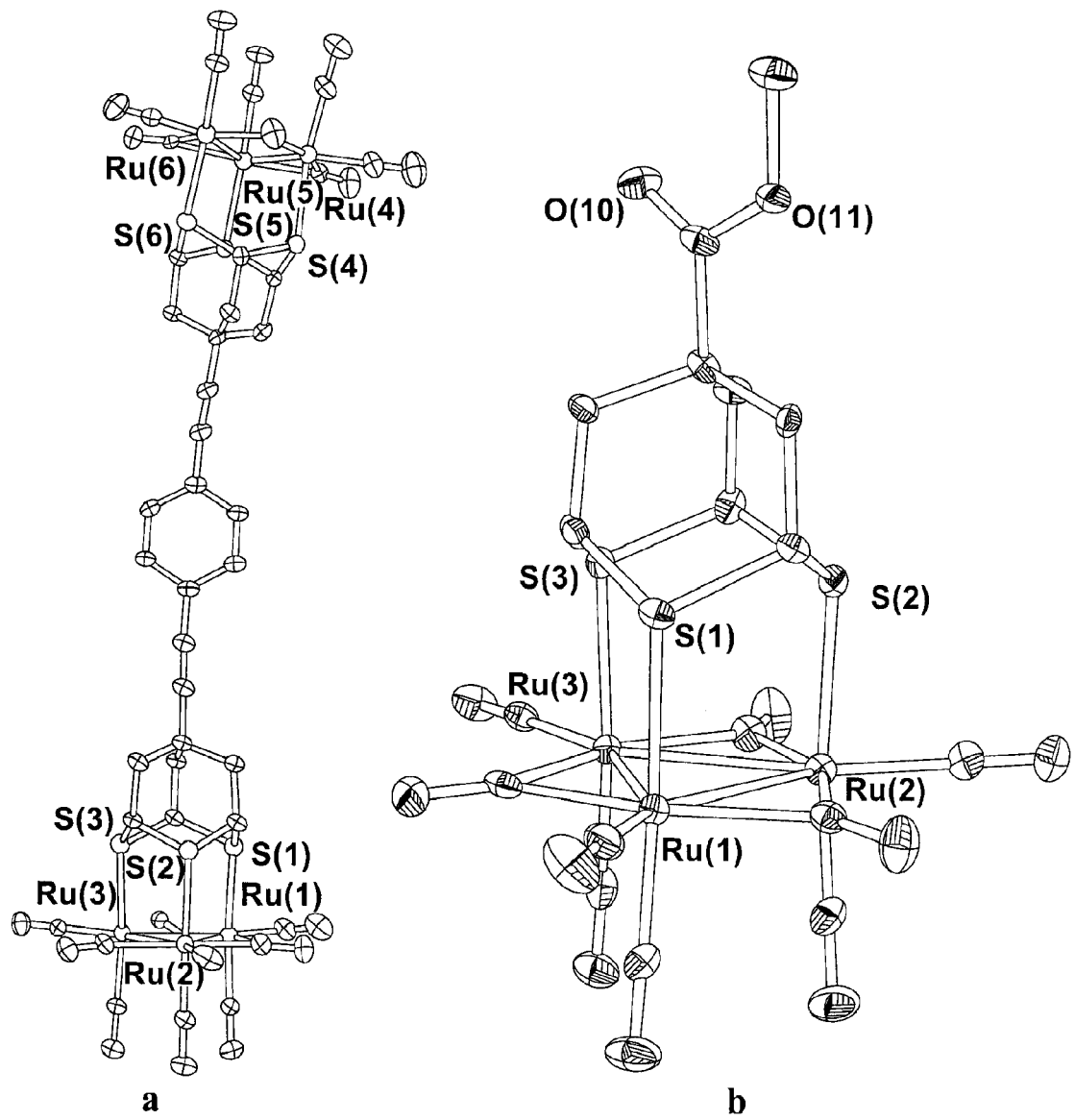
FIG. 5a is an X-ray crystal structure of an illustrative embodiment of a 2,4,9-trithiatricyclo(3.3.1.1)decane anchor-based molecular wire.
FIG. 5b is an x-ray crystal structure of a ruthenium cluster complex of methyl-2,4,9-trithiaadamantane-7-carboxylate.
Figure 6:
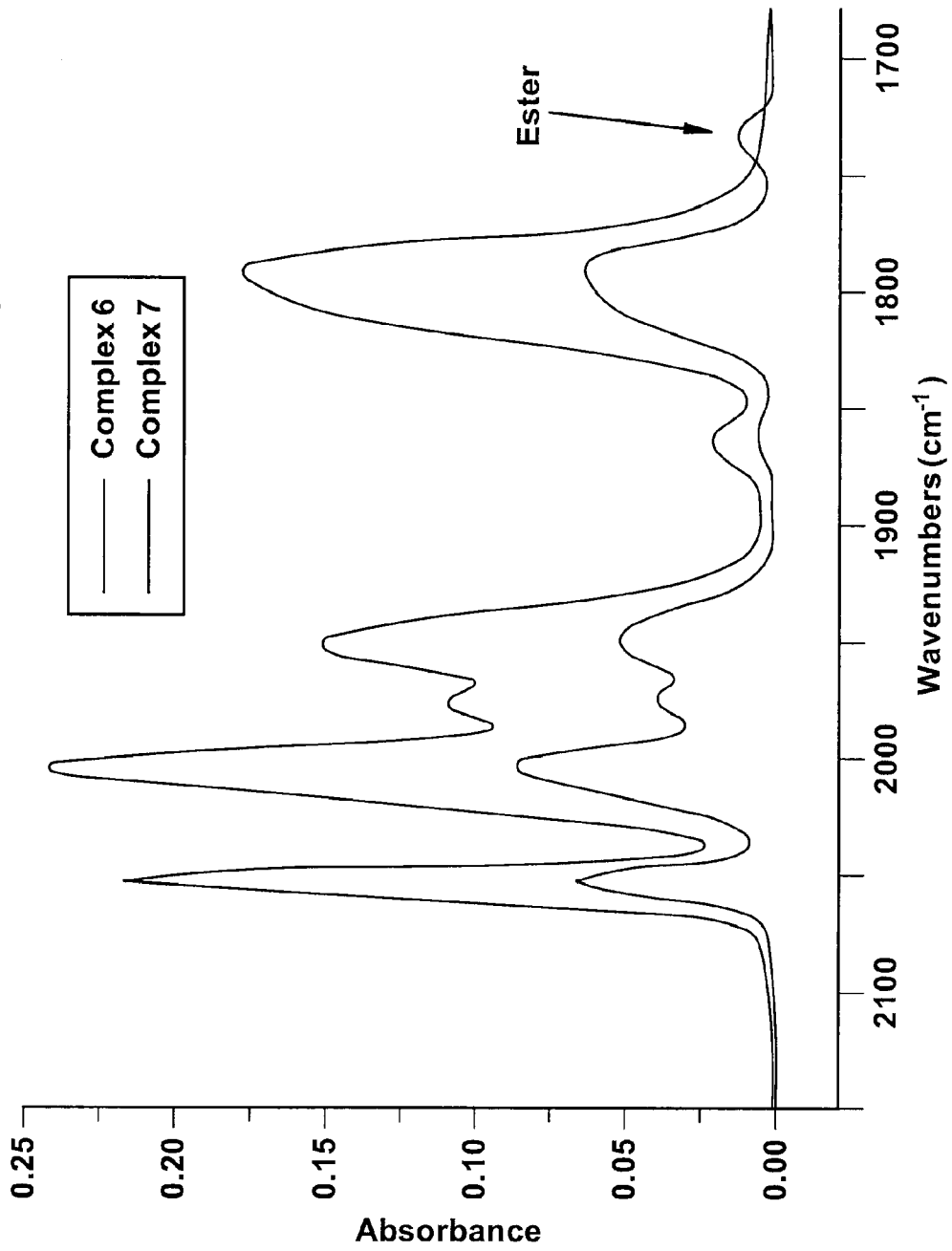
FIG. 6 is a view of the v(CO) absorption bands for complex (6) and complex (7) shown in FIGS. 5a and 5b, respectively.

While investigating the conductivity of the molecular wire candidate with scanning probe techniques, the coordination chemistry of the molecular tripod with transition metal clusters was also examined to gain insight of the surface binding characteristics of the molecular tripod. When (5) was allowed to react with Ru3(CO)12 in refluxing THF for 2 h, complex (6) was produced in 62% isolated yield. Similarly, a corresponding ruthenium cluster complex of methyl-2,4,9-trithiaadamantane-7-carboxylate can be produced in a comparable yield. Recrystallization of both compounds from THF/hexanes produced single crystals that were suitable for X-ray structure elucidation. From the X-ray structure elucidation, it is believed that the tripodal ligand coordinates to one face of the triruthenium cluster as shown in FIGS. 5a and 5b. The three sulfur atoms in the tripod bind axially to each ruthenium center in a mode similar to that observed in the trithane ligand of $Ru(CO)_6(\mu\text{-}CO)_3(\mu\text{-}S_3C_3H_6)$ and the benzene ring of $Ru(CO)_9(\mu_3:\eta^2:\eta^2:\eta^2\text{-}C_6H_6)$. The size of the tripod ligand closely matched the triruthenium unit; the spacing between sulfur atoms in both compounds was found to be about 3.05 Å, while the metal-metal bond distance was found to be about 2.85 Å. The spacing of metal atoms in the cluster is similar to that observed in bulk ruthenium metal, which is about 2.7 Å, thus, it is believed that these assemblies mimic bulk metal binding. The metal cluster units exhibited three carbonyl environments: terminal axial, terminal equatorial and bridging equatorial. The presence of bridging carbonyls, which are more efficient π-electron acceptors than terminal carbonyls, is believed to be most likely due to the significantly lower π-electron acidity of the tripod ligand than CO. The solution phase IR spectra of the compounds represented in FIGS. 5(a) and 5(b) substantially agree with the observed CO coordination modes (FIG. 2).

Figure 7:
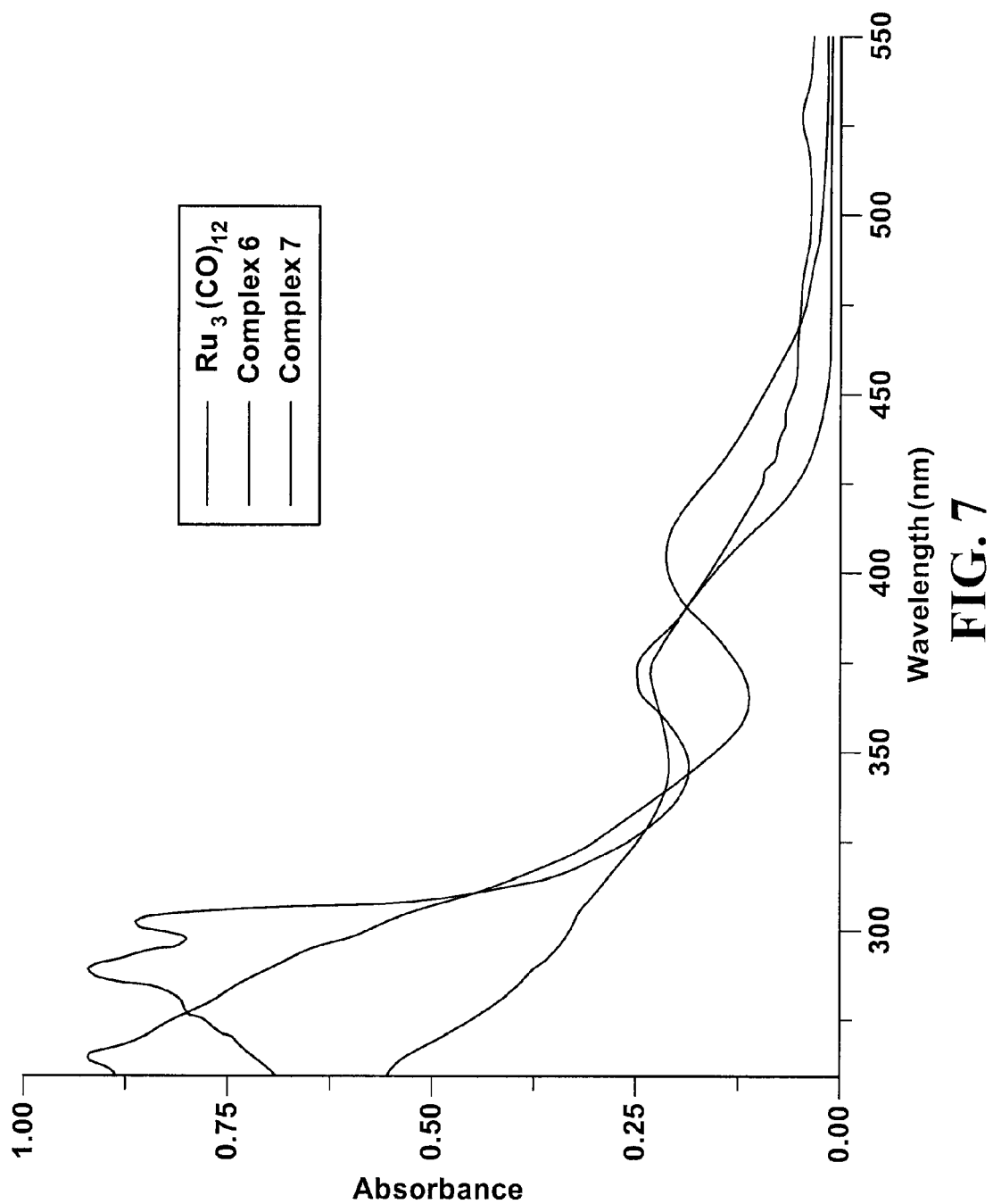
FIG. 7 is a UV-Vis spectra of the triruthenium cluster complexes shown in FIGS. 5a and 5b.
Figure 8:
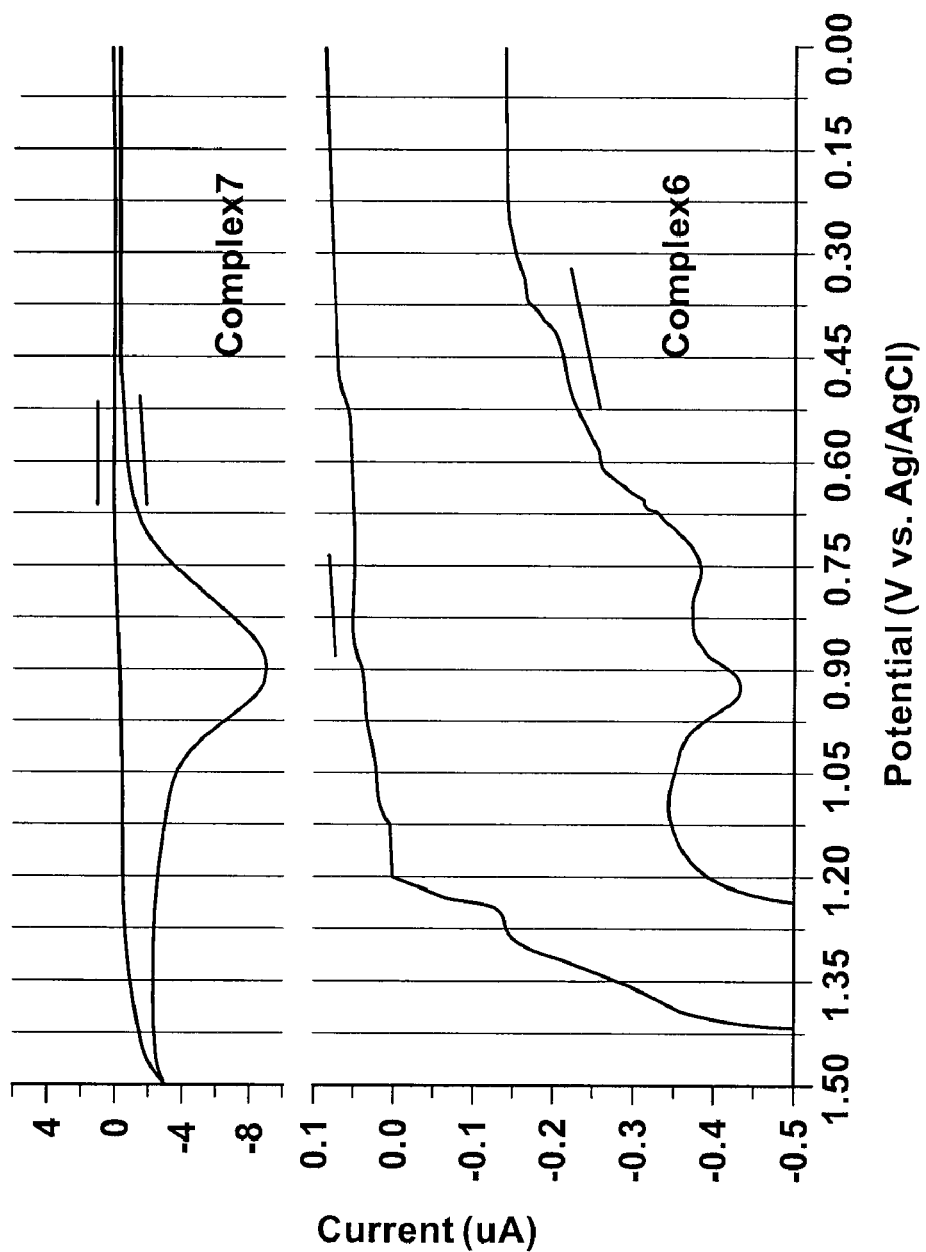
FIG. 8 includes cyclic voltammograms for the complexes shown in FIGS. 5a and 5b.

The structures of complex 6 and the complex represented in FIG. 5(b), (the complex represented in FIG. 5(b) also known herein as complex 7), were also confirmed by NMR (1H, 13C) and UV-Vis. The 13CNMR spectra of the structures display a single metal carbonyl resonance at about 197 ppm believed to be due at least in part to the rapid pseudo rotation between the terminal and bridged ligands. This single-carbonyl resonance splits into two peaks at about 197 and about 195 ppm at about −55° C. Further, both structures display a UV-vis absorption band at about 370 nm for the $Ru_3$ metal cluster, which is blue-shifted from 404 nm observed for $Ru_3(CO)_{12}$ as shown in FIG. 7. Alternative bridging moieties can also be incorporated to span the distance between trithiaadamantane-tripod units, and complexing molecular wire candidates can also be formed from alternative metal ions or clusters at the termini without departing from the scope of the present invention. For example, preliminary cyclic voltammogram ("CV") experiments showed that there are two peaks separated by 180 mV for complex 6, which correspond to sequential irreversible oxidation of the $Ru_3$ clusters shown in FIG. 8.

In comparison, the complex represented in FIG. 5(b) displays only one peak at this particularly region. The large separation in the oxidation potential of the two bridged clusters can be plausibly attributed to electronic coupling between the metal clusters through the molecular wire candidate.

Methyl 7-hydroxycarbonyl-2,4,9-trithiaadamantane

A solution of 5 grams of methyl triallyl acetate in 100 milliliters freshly distilled methylenechloride was stirred and cooled to −78° C. in a dry-ice acetone bath. Ozone was bubbled through the cooled mixture until a light-blue color persisted. The ozone line was then disconnected and the excess ozone was removed by argon flow for 10 minutes. 6.0 grams dimethyl sulfide was added to the reaction mixture at −78° C. The mixture was slowly warmed up to the ambient temperature. The mixture was then concentrated via rotary evaporation. To this mixture, 100 milliliters of methylenechloride, 28.0 grams of Lawesson's reagent, and 100 milliliters of neat $BF_3.Et_2O$ were added respectively. The mixture was then refluxed for 100 hours. Additional methylenechloride was added (100 mL). The mixture was washed using conventional techniques with 0.2 M potassium carbonate three times. The organic layer was dried over magnesium sulfate and evaporated. The resulting mixture was purified by column chromatography on silica gel using 30% methylenechloride in hexane to give pure methyl 7-hydroxycarbonyl-2,4,9-trithiaadamantane (35-40% yield; melt point 149° C.-151° C.).

7-hydroxymethyl-2,4,9-trithiaadamantane

A flame-dried, 25 mL round-bottomed flask equipped with a Teflon-coated magnetic bar and a septum with an argon inlet was charged with 270 mg (1.10 mmol) of 2,4,9-Trithia-tricyclo[3.3.1.13,7]decane-7-carboxylic acid methyl ester and 5 mL of dry toluene. Cooled by an ice bath, the solution was charged with 1.60 mL of 1.5 M (2.3 mmol) diisobutyl aluminum hydride in hexane. The solution was stirred at 0° C. until the complete consumption of the starting material was observed (monitored by TLC). The solution was quenched by 2 mL of methanol and allowed to warm to the ambient temperature. The filtration through a celite filter cake gave 240 mg (97%) of 7-hydroxymethyl-2,4,9-trithiaadamantane.

7-carbonyl-2,4,9-trithiaadamantane

To an acetone-ice cooled three-necked, 25 mL, round bottomed flask equipped with a dropping funnel, was charged with 0.07 mL of oxalyl chloride (0.83 mmol) dissolved in 3 ml of dichloromethane. Dimethyl sulfoxide (0.12 mL, 1.66 mmol) was charged into a dropping funnel and added dropwise to a stirred solution of oxalyl chloride. The solution mixture was stirred at −78° C. for 5 minutes. 7-hydroxymethyl-2,4,9-trithiaadamantane dissolved in 5 mL of dichloromethane and a small amount of dimethyl sulfoxide was charged into a dropping funnel and added dropwise to a solution mixture of dimethyl sulfoxide and oxalyl chloride. The reaction was stirred at −78° C. for 45 minutes (reaction monitored by TLC). Triethylamine (5 mL) was added to a stirred solution. The solution was allowed to warm up to the room temperature. Water (20 mL) was added to a solution and the mixture was extracted with 10 mL dichloromethane three times. The product was quickly used for the next synthesis because of its poor stability.

7-ethynyl-2,4,9-trithiaadamantane

To an ice-cooled solution of sodium hydride in dry toluene, (2-oxo-propyl)-phosphonic acid dimethyl ester was added slowly. The solution mixture was stirred for 1 hour. Methanesulfonyl azide, prepared by the reaction of methanesulfonyl chloride and sodium azide, dissolved in dry toluene and dry tetrahydrofuran was added to a solution. The mixture was allowed to slowly warm up to the ambient temperature and stirred for additional 2 hours. Filtration through a celite filter cake gave yellowish oil of (1-Diazo-2-oxo-propyl)-phosphonic acid dimethyl ester, which was used for the next step without any further purification.

To a solution of aldehyde in 2 mL of dry methanol and potassium carbonate (2 equivalents) was added a solution of (1-Diazo-2-oxo-propyl)-phosphonic acid dimethyl ester (1.2 equivalents) in dry methanol. The solution was stirred for 12 hours. A 20 mL portion of dichloromethane was added to a solution. The resulting organic solution was washed with apportion of 20 mL of 5% sodium bicarbonate. After the evaporation of the solvent, the crude product was purified by column chromatography to yield 7-ethynyl-2,4,9-trithiaadamantane in 75-80% yield.

In light of the foregoing, it should be evident that the present invention, which provides: 7-ethynyl-2,4,9-trithiaadamantane, a method for its manufacture, and a method for its use as a tripodal surface anchor substantially improves the art. While, in accordance with the patent statutes, only the preferred embodiments of the present invention have been described in detail hereinabove, the present invention is not to be limited thereto or thereby. Rather, the scope of the invention shall include all modifications and variations that fall within the scope of the attached claims.

What is claimed is:

1. A molecular wire composition comprising a molecular wire having a trithiaadamantane surface anchor.

2. A molecular wire having the formula:

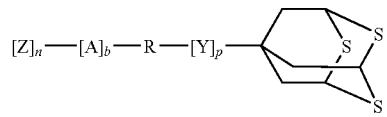

wherein A and Y are independently selected chemical functionalities;
wherein p is 0 or 1;
wherein b is 0 or an integer greater than or equal to 1;
wherein R is a compound that is capable of transferring a signal;
wherein Z is a surface anchor; and
wherein n is 0 or an integer greater than or equal to 1.

3. The molecular wire of claim 2, wherein Z is selected from the group consisting of:

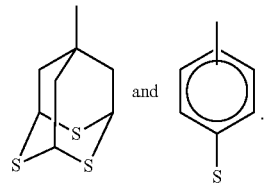

4. The molecular wire of claim 2 wherein A and Y are independently selected from the group consisting of ethynyl and carboxylate.

5. The molecular wire of claim 2, wherein the wire is selected from the group consisting of:

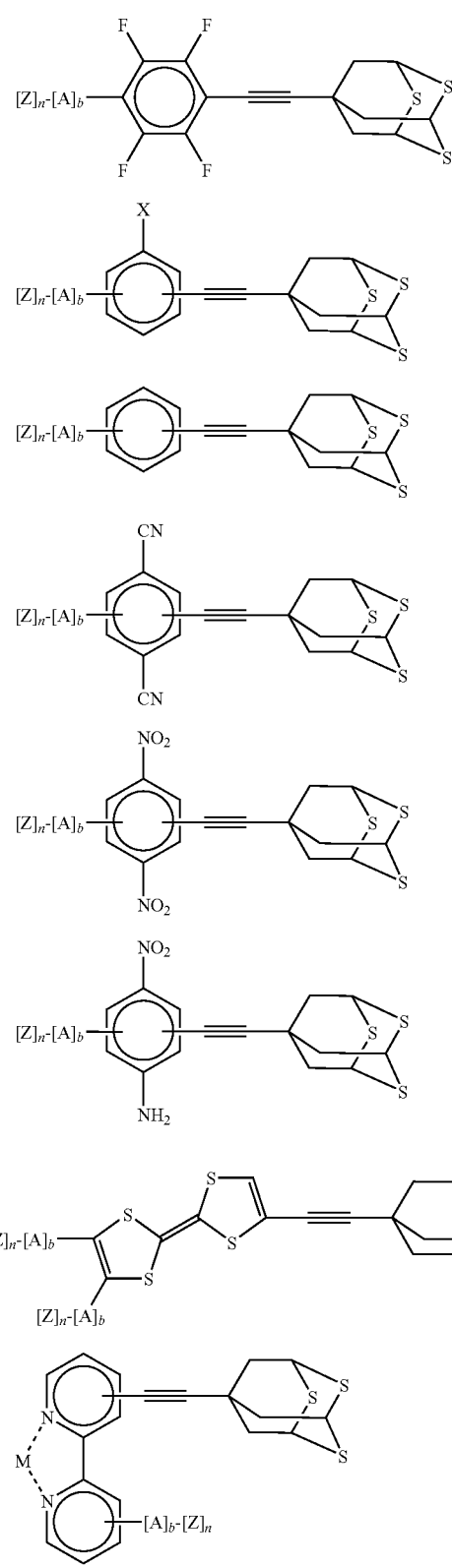

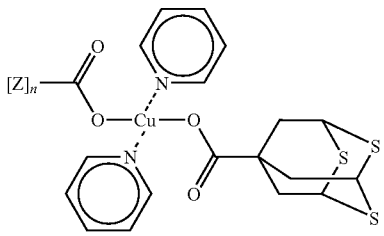

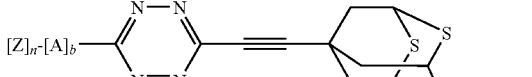

wherein A is a chemical functionality;
wherein b is 0 or an integer greater than or equal to 1;
wherein Z is a surface anchor;
wherein n is 0 or an integer greater than or equal to 1;
wherein M is a metallic element; and
wherein X is a halogen.

6. The molecular wire of claim 5, wherein M is selected from the group consisting of platinum, palladium, and copper.

7. The molecular wire of claim 5, wherein X is selected from the group consisting of fluorine, chlorine, bromine, and iodine.

8. The molecular wire of claim 5, wherein Z is selected from the group consisting of:

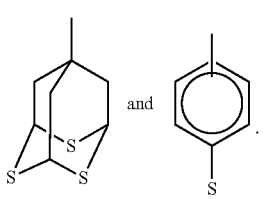

9. The molecular wire of claim 5, wherein A is ethynyl or ester.

10. A method for manufacturing a molecular wire comprising the step of chemically bonding, either directly or indirectly, trithiaadamantane to a compound that is capable of transferring a signal.

11. The method of claim 10, wherein the signal is electronic.

12. A molecular wire produced by the method of claim 10.

13. A composition comprising:
a molecular wire having a trithiaadamantane surface anchor, wherein the molecular wire also has an insulation coating.

14. The composition of claim 13, wherein the insulation coating is β-cyclodextrin.

* * * * *